United States Patent
Zysman-Colman et al.

(10) Patent No.: US 10,236,454 B2
(45) Date of Patent: Mar. 19, 2019

(54) LUMINESCENT COMPLEXES AND DISPLAY DEVICES

(71) Applicant: University Court of the University of St. Andrews, St. Andrews (GB)

(72) Inventors: Eli Zysman-Colman, Fife (GB); Adam Henwood, Fife (GB)

(73) Assignee: UNIVERSITY COURT OF THE UNIVERSITY OF ST ANDREWS (GB)

( * ) Notice: Subject to any disclaimer, the term of this patent is extended or adjusted under 35 U.S.C. 154(b) by 0 days.

(21) Appl. No.: 14/944,427

(22) Filed: Nov. 18, 2015

(65) Prior Publication Data

US 2016/0141523 A1    May 19, 2016

Related U.S. Application Data

(60) Provisional application No. 62/081,322, filed on Nov. 18, 2014.

(51) Int. Cl.
| | |
|---|---|
| *H01L 51/00* | (2006.01) |
| *C07F 15/00* | (2006.01) |
| *C09K 11/06* | (2006.01) |
| *H01L 51/50* | (2006.01) |

(52) U.S. Cl.
CPC ...... *H01L 51/0085* (2013.01); *C07F 15/0033* (2013.01); *C09K 11/06* (2013.01); *C09K 2211/1007* (2013.01); *C09K 2211/1029* (2013.01); *C09K 2211/1044* (2013.01); *C09K 2211/185* (2013.01); *H01L 51/5012* (2013.01)

(58) Field of Classification Search
CPC .................................................. C07F 15/033
See application file for complete search history.

(56) References Cited

PUBLICATIONS

Rasmussen. Journal of the American Chemical Society, 1982, 104(22), 6155-56.*
Jena. Indian Journal of Chemistry, 1999, 38a, 350-54.*
"Periodic Table", http://www.chem.qmul.ac.uk/iupac/AtWt/table.html, accessed May 24, 2017.*
Henwood. Faraday Discussions, 2014, 174, 165-182.*
Campeau et al., "A Solution to the 2-Pyridyl Organometallic Cross-Coupling Problem: Regioselective Catalytic Direct Arylation of Pyridine N-Oxides," Journal of American Chemical Society, 2005, vol. 127, pp. 18020-18021.
Demas et al., "The Measurement of Photoluminescence Quantum Yields. A Review," The Journal of Physical Chemistry, 1971, vol. 75(8), pp. 991-1024.
Fery-Forgues et al., "Are Fluorescence Quantum Yields So Tricky to Measure? A Demonstration Using Familiar Stationery Products," Journal of Chemical Education, 1999, vol. 176(9), pp. 1260-1264.
He et al., "Toward Highly Efficient Solid-State White Light-Emitting Electrochemical Cells: Blue-Green to Red Emitting Cationic Iridium Complexes with Imidazole-Type Ancillary Ligands," Advanced Functional Materials, 2009, vol. 19, pp. 2950-2960.
Kozhevnikov et al., "Cyclometalated Ir(III) Complexes for High-Efficiency Solution-Processable Blue PhOLEDs," Chemistry of Materials, 2013, vol. 25, pp. 2352-2358.
Ladouceur et al., "Strongly Blue Luminescent Cationic Iridium(III) Complexes with an Electron-rich Ancillary Ligand: Evaluation of Their Optoelectronic and Electrochemiluminescence Properties," European Journal of Inorganic Chemistry, 2013, pp. 5329-53443.
Melhuish, "Quantum Efficiencies of Fluorescence of Organic Substances: Effect of Solvent and Concentration of the Fluorescent Solute," Journal of Physical Chemistry, 1961, vol. 65(2), pp. 229-235.
Nonoyama, "Benzo[h]guinolin-10-yl-N Iridium (III) Complexes," Bulletin of the Chemical Society of Japan, 1974, vol. 47(3), pp. 767-768.
Pavlishchuk et al., "Conversion constants for redox potentials measured versus different reference electrodes in acetonitrile solutions at 25° C.," Inorganica Chimica Acta, 2000, vol. 298, pp. 97-102.
Phan et al., "Heteroleptic Fell Complexes of 2,2'-Biimidazole and Its Alkylated Derivatives: Spin-Crossover and Photomagnetic Behavior," Chemistry, A European Journal, 2012, vol. 18, pp. 15805-15815.
Sengottuvelan et al., "Tuning Photophysical and Electrochemical Properties of the Heteroleptic Cationic Iridium(III) Complexes Containing Substituted 2-Phenylquinoxaline and Biimidazole," Bulletin Korean Chemical Society, 2010, vol. 31(8), pp. 2309-2314.
Thummel et al., "Bridged Derivatives of 2,2'-Biimidazole," Journal of Organic Chemistry, 1989, vol. 54(13), pp. 3057-3061.
Xiao et al., "Synthesis of 2,2¢-Biimidazolium-Based Ionic Liquids: Use as a New Reaction Medium and Ligand for Palladium-Catalyzed Suzuki Cross-Coupling Reactions," Journal of Organic Chemistry, 2005, vol. 70, pp. 3072-3078.
Yun et al., Blue Emitting Cationic Iridium Complexes Containing Two Substituted 2-Phenylpyridine and One 2,2'-Biimidazole for Solution-processed Organic Light-Emitting Diodes (OLEDs), Bulletin Korean Chemical Society, 2012, vol. 33(11), pp. 3645-3650.

* cited by examiner

*Primary Examiner* — Noble E Jarrell
(74) *Attorney, Agent, or Firm* — Sheridan Ross P.C.

(57) ABSTRACT

Cationic iridium III complexes including a ligand according to formula I are provided. The linking group Z is a hydrocarbylene linking group comprising at least two carbon atoms in a chain. Ligands according to formula I have increased rigidity about the central bond linking the two five membered rings by virtue of the linking group Z, when compared to previous biimidazole related ligands. Increased photoluminescence quantum yield may been obtained in cationic iridium III complexes provided with these ligands.

28 Claims, 3 Drawing Sheets

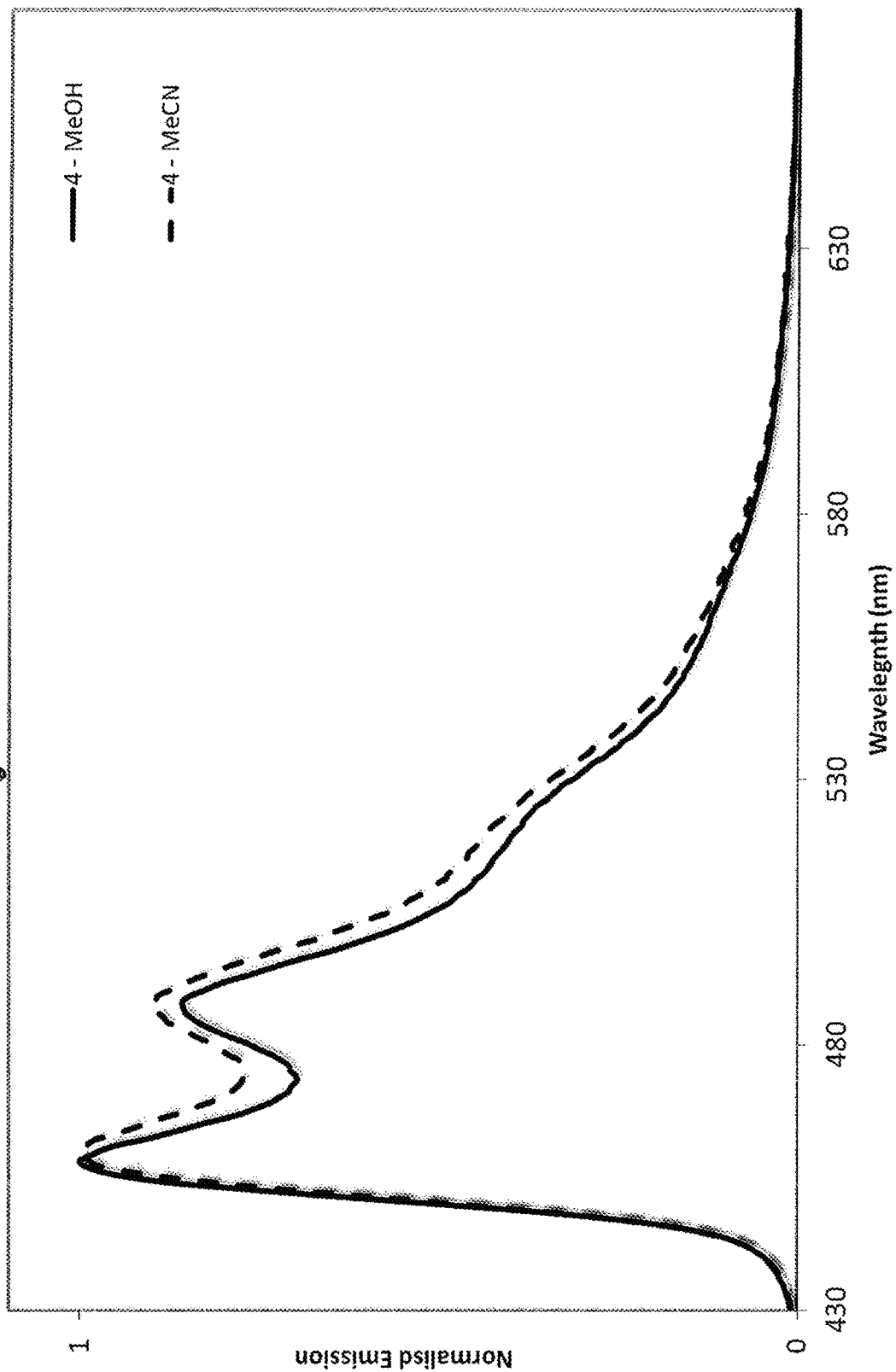

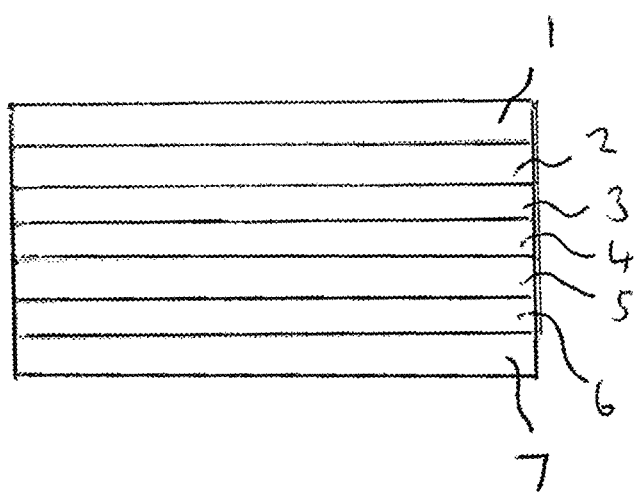

LUMINESCENT COMPLEXES AND DISPLAY DEVICES

CROSS-REFERENCE TO RELATED APPLICATIONS

This application claims the benefit of U.S. Provisional Application No. 62/081,322 filed Nov. 18, 2014, the entire contents of which is incorporated herein by reference.

FIELD OF THE INVENTION

The present invention is directed to the provision of luminescent iridium complexes and ligands for luminescent iridium complexes. The invention is also directed to light emitting electrochemical cells (LEECs) that make use of the iridium complexes.

BACKGROUND TO THE INVENTION

For many years Organic Light-Emitting Diodes (OLEDs) have been touted as the technology that will usurp conventional fluorescent tubes as the market's dominant lighting source, owing to their use of environmentally benign, relatively cheap emissive materials and their capacity to achieve external quantum efficiencies of 100%.

However, in spite of these desirable features, OLEDs have struggled to attain universal marketability as the solid-state lighting (SSL) technology of choice. The emissive materials employed are incapable of effecting balanced charge injection and mobility, thus necessitating the encapsulation of low work function, air-reactive electrodes within complex multilayer compositions. Fabrication of such sensitive devices thus typically requires vacuum sublimation—a process which is both labor- and cost-intensive, and requires thermally stable, non-ionic materials, which limits the choice of organometallic triplet harvesters that might be used.

A promising alternative lighting technology to OLEDs is Light-Emitting Electrochemical Cells (LEECs). By using charged materials they confer many of the same advantages but they allow for the circumvention of the arduous vacuum sublimation process. Processing is instead carried out by solution printing, using air-stable high work function electrodes in a single- or two-layer device architecture, making large-area artificial illumination a very real possibility.

Two classes of emitter materials are typically employed:
1) a mixture of conjugated polymer, ion transport material and inorganic salt such as LiOTf; or
2) an ionic Transition Metal Complex (iTMC). Of the different families of iTMCs, by far the most widely studied and exciting class of emitters for LEECs are heteroleptic cationic iridium(III) complexes, of the form $[Ir(C\hat{}N)_2(N\hat{}N)]^+$, where $C\hat{}N$ is a monoanionic cyclometalating bis(chelate) and $N\hat{}N$ is a neutral diimine ancillary ligand. More generally, the term $C\hat{}N$ means a ligand coordinating by carbon and by nitrogen to the metal (iridium in this example). The term $N\hat{}N$ means a ligand datively coordinating by two nitrogen atoms to the metal. A typical $C\hat{}N$ ligand is 2-phenylpyridinato.

LEECs too present their own design challenges. Issues that still require addressing for iTMC LEECs include slow turn-on times, limited device stability and poor colour quality. In particular, few examples exist of blue-emitting LEECs, which is mainly due to a shortage of deep blue, brightly emitting complexes. Blue emitters are critical both for white light emission and as a component of RGB-based pixels in displays.

Designing iridium complexes for blue emission by combining electron-deficient $C\hat{}N$ and electron-rich $N\hat{}N$ ancillary ligands, has been met with varying degrees of success. There are now a few reported examples of deep blue emitting cationic iridium complexes in solution ($\lambda_{max}$<470 nm), but significant issues still remain regarding the brightness of these emitters.

Complexes bearing imidazole ligands have been employed in a diverse set of photo physical applications ranging from bio imaging and sensing to excited state proton-coupled electron transfer (PCET) and solid-state lighting.

Of particular interest are iridium complexes of the form $[Ir(C\hat{}N)_2(N\hat{}N)]^+$ bearing a 1H,1H'-2,2'-biimidazole (biim) $N\hat{}N$ ligand.

Kim and co-workers recently showed that combining the biim $N\hat{}N$ ligand with an electron-deficient $C\hat{}N$ ligand in $[Ir(dFpmpy)_2(biim)]^+$, where dFpmpy is 2-(2',4'-difluorophenyl)-4-methylpyridinato, could achieve deep blue emission, with emission maxima at 456 and 484 nm in DCM. However, despite such promising examples in terms of emission energy, photoluminescence quantum yields (PLQY, $\Phi_{PL}$) remain very low (Figure A below, reference 1).

FIG. A. Literature examples of cationic iridium complexes containg a biim-based $N\hat{}N$ ligand.

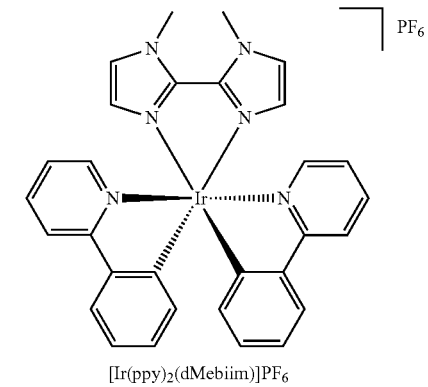

[Ir(ppy)$_2$(dMebiim)]PF$_6$
$\lambda_{max}$: 497 nm
$\Phi_{PL}$ = 5%
Adv. Funct. Mater., 2009, 19, 2950

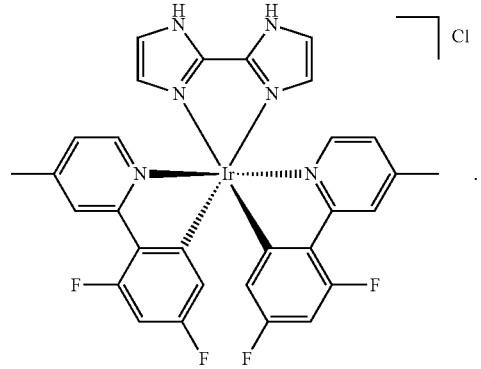

[Ir(dFpmpy)$_2$(biim)]Cl
$\lambda_{max}$: 456, 484 nm
$\Phi_{PL}$ = 10.2%
Bull. Korean Chem. Soc., 2012, 33, 3645

Accordingly there is a need to provide improved and alternative iridium complexes for use in display and lighting uses, such as in light emitting electrochemical cells (LEECs).

DESCRIPTION OF THE INVENTION

According to a first aspect the present invention provides a cationic iridium III complex including a ligand according to formula I:

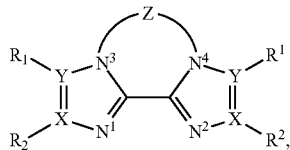

wherein nitrogen atoms $N^1$ and $N^2$ coordinate to iridium;
X and Y are independently for each occurrence selected from C or N; and either
i) $R^1$ and $R^2$ are independently for each occurrence selected from the group consisting of —H, substituted or unsubstituted primary, secondary or tertiary alkyl, that may be cyclic and may be saturated or unsaturated; substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —S(O)$_2$R, —S(O)$_2$NR, —ROC(O)NR$_2$, and ROC(O)N(R)R—,
wherein each group R when present on a substituent $R^1$ or $R^2$ is, independently for each occurrence, selected from substituted or unsubstituted alkyl, that may be cyclic and may be saturated or unsaturated, substituted or unsubstituted aryl, and substituted or unsubstituted heteroaryl, or $R^1$ and $R^2$ are absent when dictated by the valency of X or Y; or
ii) one of the pairs of adjacent $R^1$ and $R^2$ groups is fused to form a ring that may be saturated or unsaturated, substituted or unsubstituted, may contain heteroatoms and may have one or more further rings fused to it; and the other $R^1$ and $R^2$ are independently selected from the group consisting of —H, substituted or unsubstituted primary, secondary or tertiary alkyl, that may be cyclic and may be saturated or unsaturated; substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —S(O)$_2$R, —S(O)$_2$NR, —ROC(O)NR$_2$, and ROC(O)N(R)R—,
wherein each group R when present on a substituent $R^1$ or $R^2$ is, independently for each occurrence, selected from substituted or unsubstituted alkyl, that may be cyclic and may be saturated or unsaturated, substituted or unsubstituted aryl, and substituted or unsubstituted heteroaryl or are absent when dictated by the valency of X or Y; or
iii) both pairs of adjacent $R^1$ and $R^2$ groups are each fused to form a ring that may be saturated or unsaturated, substituted or unsubstituted, may contain heteroatoms and may have one or more further rings fused to it; and wherein
Z is a hydrocarbylene linking group comprising at least two carbon atoms in a chain linking $N^3$ and $N^4$, wherein Z is substituted or unsubstituted hydrocarbylene or unsaturated hydrocarbylene, optionally includes one or more heteroatoms replacing one or more carbon atoms in the hydrocarbylene chain, and optionally has one or more saturated, unsaturated or aromatic rings fused to the chain.

Where groups $R^1$ and $R^2$ in formula I are substituted or unsubstituted primary, secondary or tertiary alkyl, that may be cyclic and may be saturated or unsaturated, the alkyl group may be C1 to C10 or even C1 to C4.

Halogen substituents $R^1$ and R2 may be fluoro, chloro, bromo or iodo,

Where groups $R^1$ or $R^2$ are alkyl, aryl or heteroaryl they may be independently substituted, for example once, twice, or three times, e.g. once, i.e. formally replacing one or more hydrogen atoms of the alkyl, aryl or heteroaryl group. Examples of such substituents are substituted or unsubstituted primary, secondary or tertiary alkyl, that may be cyclic and may be saturated or unsaturated (for example C1-C10 or even C1-C4); substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —S(O)$_2$R, —S(O)$_2$NR, —ROC(O)NR$_2$, and ROC(O)N(R)R—, wherein each group R when present on a substituent is, independently for each occurrence, selected from substituted or unsubstituted alkyl, that may be cyclic and may be saturated or unsaturated, substituted or unsubstituted aryl, and substituted or unsubstituted heteroaryl.

Substituents on groups R when present may be selected from those described herein in respect of groups $R^1$ or $R^2$. Typically groups R may be a C1 to C20 or even a C1 to C10 substituted or unsubstituted alkyl, that may be cyclic and may be saturated or unsaturated. Alternatives include substituted or unsubstituted aryl, and substituted or unsubstituted heteroaryl. Further alternatives include halogen, —$CF_3$, —CN, —$NO_2$, —$NR^y_2$, —$OR^y$, —$C(O)R^y$, —$C(O)OR^y$, —$C(O)NR^y$, —$SR^y$, —$C(S)R^y$, —$S(O)R^y$, —$S(O)_2R^y$, —$S(O)_2NR^y$ wherein $R^y$ may take the same meaning as R.

By aryl is meant herein a radical formed formally by abstraction of a hydrogen atom from an aromatic compound. As known to those skilled in the art, heteroaryl moieties are a subset of aryl moieties that comprise one or more heteroatoms, typically O, N or S, in place of one or more carbon atoms and any hydrogen atoms attached thereto. Exemplary aryl substituents, for example, include phenyl, naphthyl, and fluorenyl. Aryl substituents may be substituted in the same fashion as discussed above for groups $R^1$ or $R^2$. Exemplary heteroaryl substituents, for example, include furanyl, thiophenyl, pyrrolyl, oxazolyl, thiazolyl, imidazolyl, isoxazolyl, isothiazolyl, pyrazolyl, pyridinyl, pyrazinyl, pyrimidinyl, triazinyl, pyryliumyl, benzo[b]furanyl, benzo[b]thiophenyl, indolyl, 2H-isoindolyl, benzothiazolyl, benzothiophenyl and substituted forms of these.

Where groups $R^1$, $R^2$ or R are cycloalkyl they may be for example cyclohexyl or cyclopentyl. The cyclohexyl or cyclopentyl groups if present may be saturated or unsaturated and may be substituted as described above.

Where adjacent $R^1$ and $R^2$ groups in formula I are fused to form a ring, the ring may be for example a five or six membered ring that may be aromatic or heteroaromatic and may be substituted. Further rings may be fused to the ring formed between $R^1$, $R^2$, X and Y. Where X and Y forming part of the ring are carbon, examples of aromatic rings that may be formed can include substituted or unsubstituted benzene, naphthalene, anthracene, pyrene and fluorene.

Examples of heteroaromatic rings that may be formed by fusion of $R^1$ and $R^2$ include substituted or unsubstituted furan, thiophene, pyrrole, oxazole, thiazole, imidazole, isoxazole, isothiazole, pyrazole, pyridine, pyrazine, pyrimidine, triazine, pyrylium, benzo[b]furan, benzo[b]thiophene, indole, 2H-isoindole, benzothiazole and benzothiophene. The fused rings may be substituted with one or more substituents of the same types as discussed above in respect of $R^1$ or $R^2$ substituents when they are not fused. The fused heteroaromatic ring may fuse to X and Y at any bond consistent with valence considerations. The fused ring may have X and/or Y of formula I as heteroatoms where valence properties for the heteroatom allow it.

Ligands according to formula I have increased rigidity about the central bond linking the two five membered rings by virtue of the linking group Z, when compared to previous biimidazole related (N^N) ligands. Increased photoluminescence quantum yield (PLQY, $\Phi_{PL}$) has been obtained in cationic iridium III complexes provided with these ligands.

The linking group Z may take the general form:

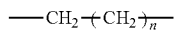

wherein n is from 1 to 5 and optionally contains one or more unsaturations and wherein one or more of the H may be replaced for example by a group selected from the group consisting of substituted or unsubstituted primary, secondary or tertiary alkyl, that may be cyclic and may be saturated or unsaturated; substituted or unsubstituted aryl or heteroaryl, halogen, —CF$_3$, —CN, —SF$_5$, —SO$_3$, —S(O)R, —NO$_2$, —NR$_2$, —OR, —C(O)R, —C(O)OR, —C(O)NR, —SR, —C(S)R, —S(O)$_2$R, —S(O)$_2$NR, —ROC(O)NR$_2$, and ROC(O)N(R)R—, wherein each group R when present is, independently for each occurrence, selected from substituted or unsubstituted alkyl, that may be cyclic and may be saturated or unsaturated, substituted or unsubstituted aryl, and substituted or unsubstituted heteroaryl, i.e. the substituents may take the form of those discussed herein with respect to groups $R^1$, $R^2$ and R as discussed with respect to formula I. The group Z may be unsaturated, having one or more double bonds and/or one or more triple bonds. Additionally or alternatively one or more saturated, unsaturated or aromatic rings may be fused to the hydrocarbylene chain of group Z. Fused rings may be substituted or unsubstituted and may contain heteroatoms.

Thus linking groups Z may take the form of any one of the following;

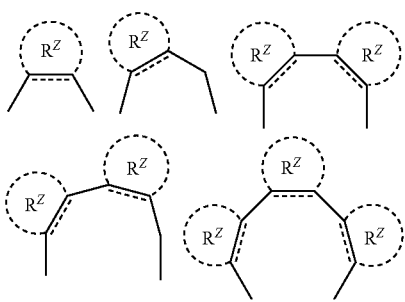

wherein dashed lines in the carbon chain represent, independently for each occurrence, optional unsaturation; and each $R^z$ indicated by dashed part circle is, independently for each occurrence, an optionally present ring of from 3 to 6 atoms.

Rings $R^z$ when present may be saturated, unsaturated, aromatic or heteroaomatic. The rings $R^z$ may be substituted or unsubstituted. If substituted one or more H of a ring $R^z$ may be replaced for example by a substituent selected from the group consisting of substituted or unsubstituted primary, secondary or tertiary alkyl, that may be cyclic and may be saturated or unsaturated; substituted or unsubstituted aryl or heteroaryl, halogen, —CF$_3$, —CN, —SF$_5$, —SO$_3$, —S(O)R, —NO$_2$, —NR$_2$, —OR, —C(O)R, —C(O)OR, —C(O)NR, —SR, —C(S)R, —S(O)$_2$R, —S(O)$_2$NR, —ROC(O)NR$_2$, and ROC(O)N(R)R—, wherein each group R when present is, independently for each occurrence, selected from substituted or unsubstituted alkyl, that may be cyclic and may be saturated or unsaturated, substituted or unsubstituted aryl, and substituted or unsubstituted heteroaryl, i.e. the substituents may take the form of those discussed herein with respect to groups $R^1$, $R^2$ and R as discussed with respect to formula I.

Rings $R^z$ when present may for example be saturated, C3 to C6, unsaturated C3 to C6 with one or more double bonds present at any position allowable by valence considerations or aromatic (e.g. phenyl). Aromatic or heteroaromatic rings $R^z$ may take the forms discussed herein with respect to rings when formed by fusion of substituents $R^1$, $R^2$ in formula I. Where a ring $R^z$ is fused to the hydrocarbylene chain Z further rings may be fused to that ring. Thus a fused 1,2 phenylene ring may have one or more further aromatic or heteroaromatic rings fused to it, to provide for example a hydrocarbylene chain Z having one or more fused naphthalene, anthracene or pyrene rings.

Examples of linking group Z can thus include the following:

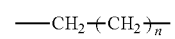

wherein n is from 1 to 5; and the unsaturated C2 to C6 groups of Scheme 1 below, including the C2 to C6 groups where one or more benzene rings (1,2-phenylene rings) are fused to the carbon chain.

Scheme 1

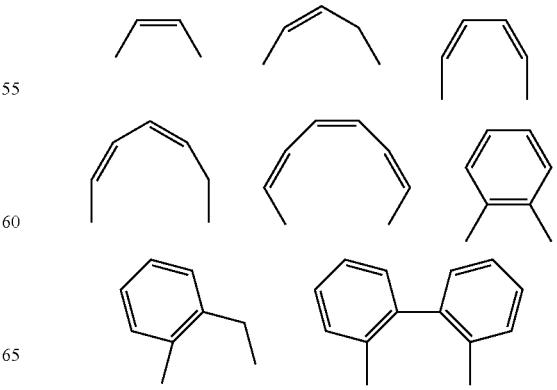

-continued

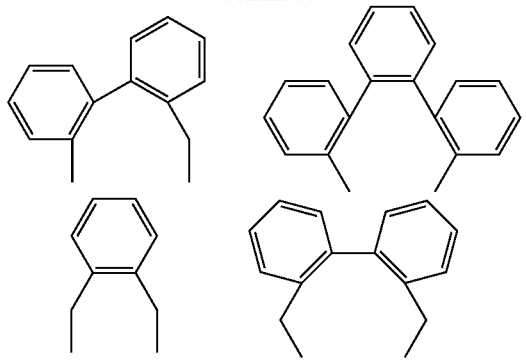

More generally it will be appreciated that where the hydrocarbylene chain of groups Z is long enough to allow more than one location of unsaturation or fusion of a ring, not all may be utilised. For example where the hydocarbylene chain is C6 there may be one, two or three double bonds provided thus:

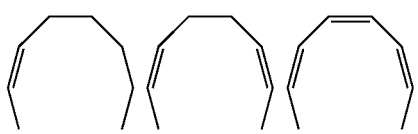

and the location on the chain of an unsaturation such as a double bond may be selected as desired where there is more than one position possible. For example:

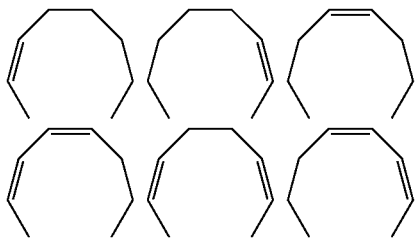

are possible with a C6 hydrocarbylene linking group and one or two double bonds.

Fused rings included in a hydrocarbylene group Z may include any one or more of cyclopentane-1,3-diyl, cyclopentane-1,2-diyl; cyclohexane-1,2-diyl, cyclohexane-1,3-diyl, cyclohexane-1,4-diyl, 1,2-phenylene, 1,3-phenylene and 1,4-phenylene and substituted derivatives thereof.

Where the hydrocarbylene chain Z includes one or more heteroatoms in the chain, it will still include at least one carbon atom. Thus a two carbon hydrocarbylene chain Z may have one carbon atom replaced by a heteroatom. Typically only one carbon atom in a chain Z may be replaced by a heteroatom, but other options are possible with longer chain length. A three carbon hydrocarbylene chain Z may have one or two carbon atoms replaced by heteroatoms. Heteroatoms may be selected, independently for each occurrence, from the group consisting of N, O and S. Thus examples of a hydrocarbylene chain substituting one O for carbon may be —$CH_2$—O— or —$CH_2$—O—$CH_2$— or —$CH_2CH_2$O—.

Substituents $R^1$ and $R^2$ in a ligand according to formula I may all be —H. Where an adjacent X and Y are carbon, one or both $R^1$ and $R^2$ may be fused to form a benzene ring, that may be substituted. Thus examples of compounds of formula I include structures such as found in formulas II, III or IV:

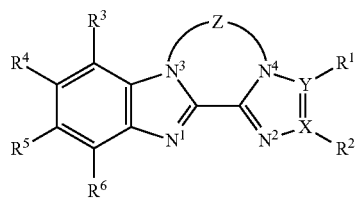

II

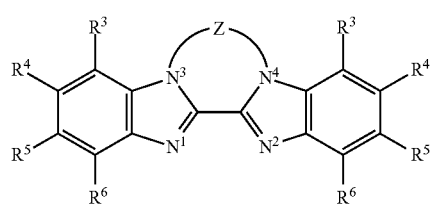

III

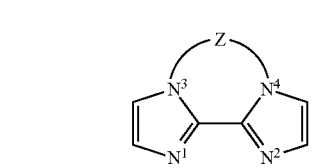

IV wherein Z, X, Y and $R^1$ and $R^2$ have the same meaning as before and wherein each $R^3$, $R^4$, $R^5$ and $R^6$ is independently for each occurrence selected from the same group of options discussed above with respect to $R^1$ and $R^2$. Each $R^3$, $R^4$, $R^5$ and $R^6$ may be H. Thus formulas IIa and IIIa are contemplated and, for example, $R^1$ and $R^2$ in formula IIa may be H:

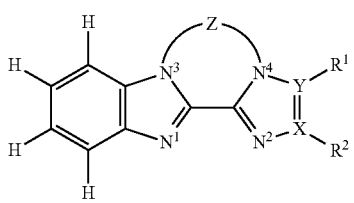

IIa

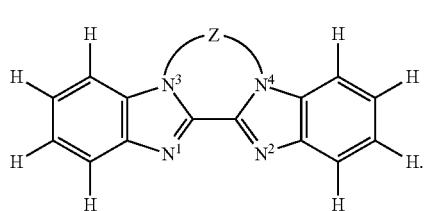

IIIa

As with groups $R^1$ and $R^2$, one or more pairs of adjacent $R^3$, $R^4$, $R^5$ and $R^6$ groups may be fused to form a ring that may be saturated or unsaturated, substituted or unsubstituted, may contain heteroatoms and may have one or more further rings fused to it.

The cationic iridium III complexes of the invention include a ligand according to formula I. Thus the structure of the complexes may be as depicted in formula V below:

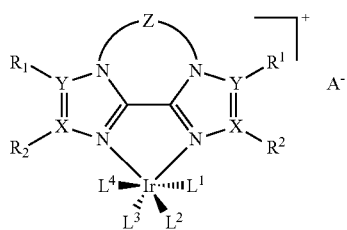

wherein A⁻ is an anion and L¹, L², L³ and L⁴ are ligands. Anion A⁻ may be selected from the group consisting of $PF_6^-$ halide, $BF_4^-$, $BR^x_4{}^-$, $OTf^-$, $OTs^-$, $SbX_6^-$ $NTf_2^-$ $NO_3^-$, $CO_3^{2-}$, wherein X is halide and $R^x$ is fluoroaryl, for example 4-fluorophenyl. Two of ligands L¹, L², L³ and L⁴ are coordinating anionic ligands.

Two of ligands L¹, L², L³ and L⁴ may be fused to form a bidentate ligand; or two pairs of L¹, L², L³ and L⁴ may be fused to form two bidentate ligands.

Typically two bidentate ligands are provided in the structure of formula V and they are C^N ligands, in particular monoanionic cyclometallating bis(chelate) ligands. Conveniently both such ligands are the same, but they may be different if required to adjust the properties of the complex.

Typically they are "C^N" ligands wherein the iridium bonds to sp² carbon and (via a lone pair of electrons) to nitrogen.

Such ligands may comprise a pair of five and/or six membered heteroaromaic and/or aromatic rings bonded together.

Thus they may be C^N ligands selected from the group consisting of:

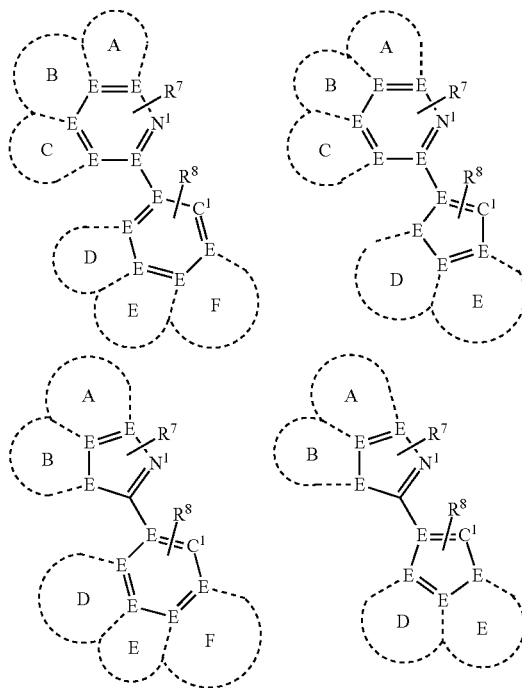

wherein nitrogen atom N¹ and carbon atom C¹ coordinate to iridium;
ring atoms E are independently for each occurrence selected from the group consisting of C, N,O, and S, where valence considerations allow, and when N may be quaternised with oxygen to form an N oxide;

dashed lines indicate optional substituted or unsubstituted fused rings A to E that may have 3 to 6 atoms that are carbon or, independently for each occurrence N,O, or S where valence considerations allow;

—R⁷ and —R⁸ represent optional replacement of at least one —H substituent, where present, of ring atoms E by a substituent independently selected for each occurrence from the group consisting of substituted or unsubstituted primary, secondary or tertiary alkyl, that may be cyclic and may be saturated or unsaturated; substituted or unsubstituted aryl or heteroaryl, halogen, —CF₃, —CN, —SF₅, —SO₃, —S(O)R, —NO₂, —NR₂, —OR, —C(O)R, —C(O)OR, —C(O)NR, —SR, —C(S)R, —S(O)₂R, —S(O)₂NR, —ROC(O)NR₂, and ROC(O)N(R)R—, wherein each group R when present on a substituent —R⁷ or —R⁸ is, independently for each occurrence, selected from substituted or unsubstituted alkyl, that may be cyclic and may be saturated or unsaturated, substituted or unsubstituted aryl, and substituted or unsubstituted heteroaryl. i.e. substituents —R⁷ and —R⁸ and substituents on rings A to E where present may be of the same types as —R¹ and —R² of formula I.

The ring atoms E may all be carbon.

Exemplary C^N ligands therefore include:

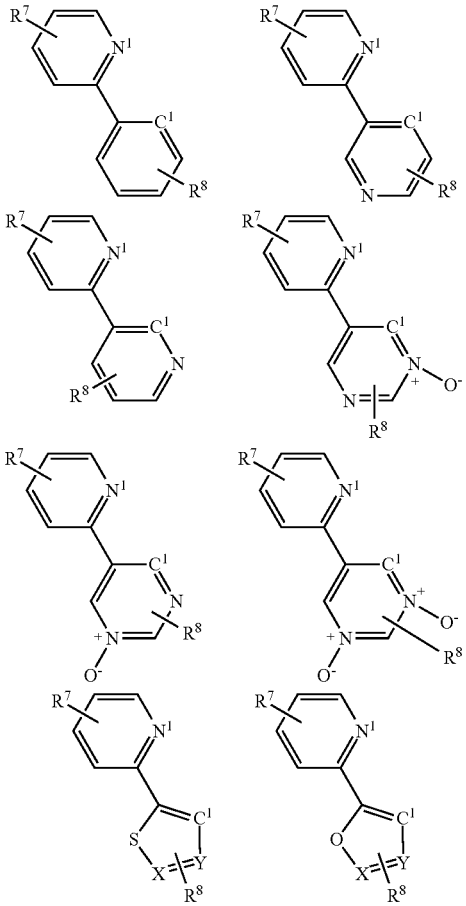

-continued

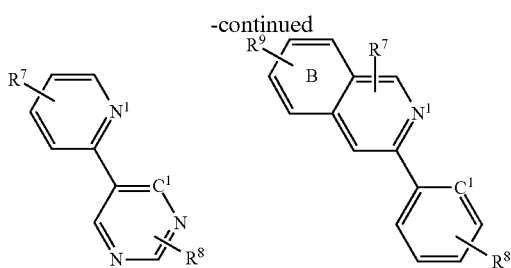

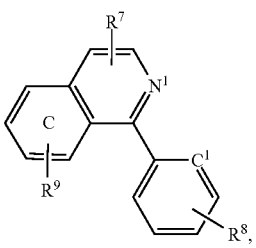

or a substituted variation may be used to provide complexes of formula V that are in accordance with formula VI or formula VII:

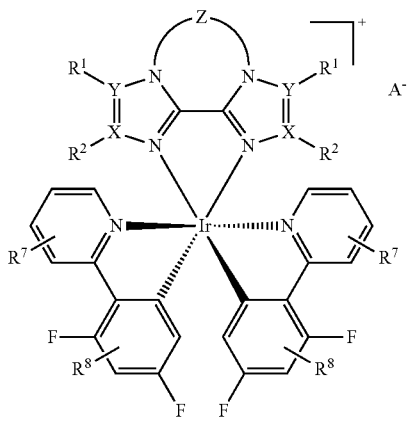

VI

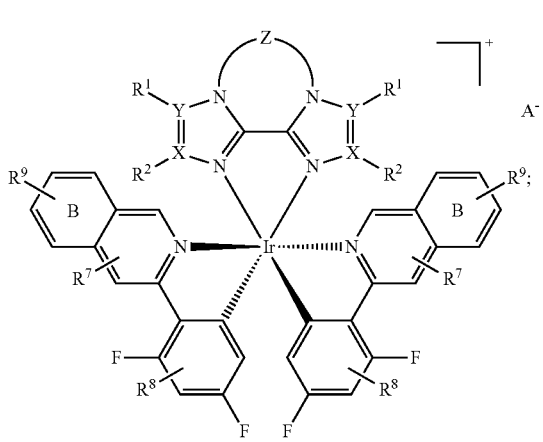

VII wherein nitrogen atom $N^1$ and carbon atom $C^1$ coordinate to iridium, X and Y have the same meaning as in formula I;
  wherein —$R^7$ represents optional replacement of one or more of the —H substituents in the ring containing nitrogen atom $N^1$ by a substituent independently selected for each occurrence from the same group of options discussed above with respect to $R^1$ and $R^2$;
  wherein —$R^9$ represents optional replacement of one or more of the —H substituents in ring B or C, when present, by a substituent independently selected for each occurrence from the same group of options discussed above with respect to $R^1$ and $R^2$;
  wherein —$R^8$ represents optional replacement of one or more of the —H substituents, when present, in the ring containing coordinating carbon atom $C^1$, by a substituent independently selected for each occurrence from the same group of options discussed above with respect to $R^1$ and $R^2$; and
  wherein one or more carbon atoms in any one or more of: the ring containing nitrogen atom $N^1$; the ring containing coordinating carbon atom $C^1$; and ring B or ring C, may be substituted by N, S or O where valence considerations allow.

Preferred substituents include —F. For example the bidentate ligand 2-(2',4'-difluorophenyl)pyridine, (dFppy):

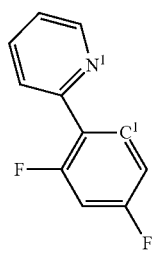

wherein Z, X, Y, $A^-$ and $R^1$, $R^2$, $R^7$, $R^8$ and $R^9$ have the same meaning as before, with $R^8$ representing optional further substitution, in addition to the two fluorine atoms shown, in the ring containing the coordinating carbon atom. Such complexes have been found to be bright emitters with good PLQY as discussed in more detail hereafter with respect to specific examples.

The structures VI and VII depicted are chiral about iridium. Enantiomers are shown to provide a convenient understanding of the spatial relationship of the ligands about iridium. Synthetic methods will generally produce a racemic mixture of both enantiomers, which may be separated if desired. Structures of iridium complexes such as VI and VII depicted herein are to be understood to refer to the racemic mixture, but with either of the two enantiomers with respect to the iridium centre also contemplated as they are available from the racemic mixture.

An example of such a bright emitter is the bright blue emitter according to formula 3, discussed in more detail hereafter:

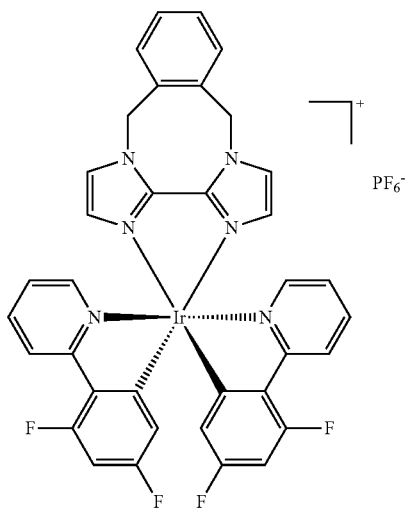

3

However although this complex has good bright blue photoluminescence properties alternative or further substitution on the N^N and/or the C^N ligands may be employed to provide further utility in terms of solubility, which is important for the processing of complexes where they are to be employed as a component of a LEEC for example. Alternative or additional functionalisation can also be used to adjust the luminescent properties.

A further example of such a bright emitter is the bright blue emitter according to formula 4, which includes 2,4,6-trimethylphenyl substituents on the C^N ligands in the ring containing the nitrogen atom that coordinates to iridium.

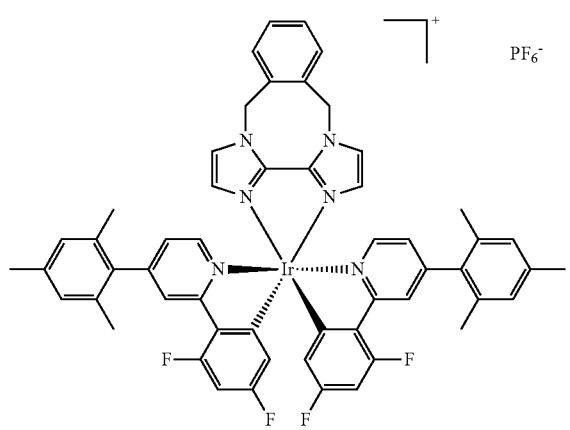

4

Complex 4 shows enhanced solubility in solvents such as methanol and acetonitrile in comparison with complex 3.

According to a second aspect the present invention provides a compound according to any one of structures I, II, III or IV. The compounds are suitable for use as ligands in the iridium complexes described herein.

The compounds of formula I and the iridium complexes of the invention may be prepared by known techniques.

For example the compounds of formula I may be made from a suitable biimidazole type substrate structure S as shown in the scheme 2 below by an alkylation procedure using a hydrocarbylene group Z provided with suitable leaving groups Le.

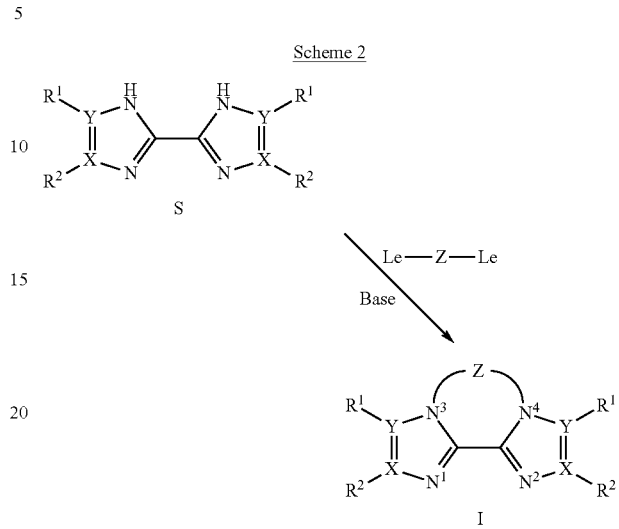

Groups $R^1$, $R^2$, Z, Y and Y have the same meaning as before. Leaving groups Le can include chloride, bromide, iodide, —OMs and —OTs. Suitable bases can include alkali metal hydroxides, such as sodium or potassium hydroxide. The reaction may be carried out in the presence of water and in a suitable polar solvent, for example DMF or acetonitrile.

After the production of an initial product according to formula I by such techniques, further modification may be carried out to any one or more of groups Z, $R^1$ and $R^2$ to provide further examples of compound of formula I.

To prepare an iridium complex including a ligand according to formula I the compound of formula I may be used to cleave an iridium dimer of the general form D as depicted generally in Scheme 3 below, where X is typically chloride. The dimer D can be prepared from iridium chloride in the known manner. Cleavage of D by an N^N ligand of formula I provides the iridium complex. The initially formed salt with anion X can be converted to a salt with a different anion X by a suitable ion exchange procedure. For example chloride can be exchanged with $PF_6$ by use of $NH_4PF_6$ as described hereafter with respect to particular examples.

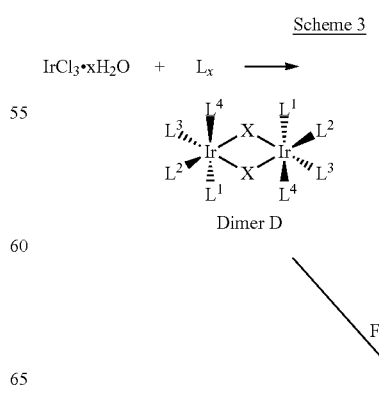

15

-continued

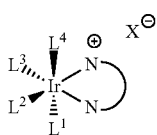

As an alternative to the use of an Iridium salt such as IrCl₃.xH₂O as precursor to the dimer D the known Iridium complex [Ir(COD)(μ-Cl)]₂ (where COD is 1,5-cyclooctadiene) may be employed.

As another alternative an iridium complex may be produced using a biimidazole type structure S (as shown in Scheme 1), as an N^N ligand. The structure S is used to make the iridium complex IrS from a dimer D. The N^N ligand can then be converted to a structure according to formula I, when already part of the iridium complex, by alkylation as shown in scheme 4.

Scheme 4

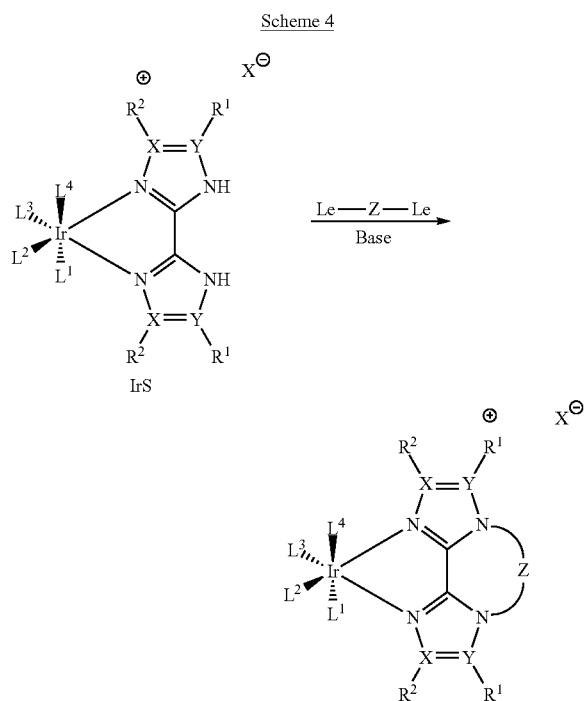

The present invention also provides a light emitting device comprising a cationic iridium III complex as described herein. The light emitting device may be a light emitting electrochemical cell (LEEC) or an organic light emitting diode (OLED) comprising a cationic iridium III complex of the invention as described herein.

BRIEF DESCRIPTION OF THE DRAWINGS

FIG. 2 shows the emission spectra of an iridium complex in different solvents; and FIG. 3 shows an Organic Light-Emitting Diode (OLED) in accordance with some embodiments.

16

DESCRIPTION OF SOME PREFERRED EMBODIMENTS AND EXPERIMENTAL RESULTS

Figure 1:
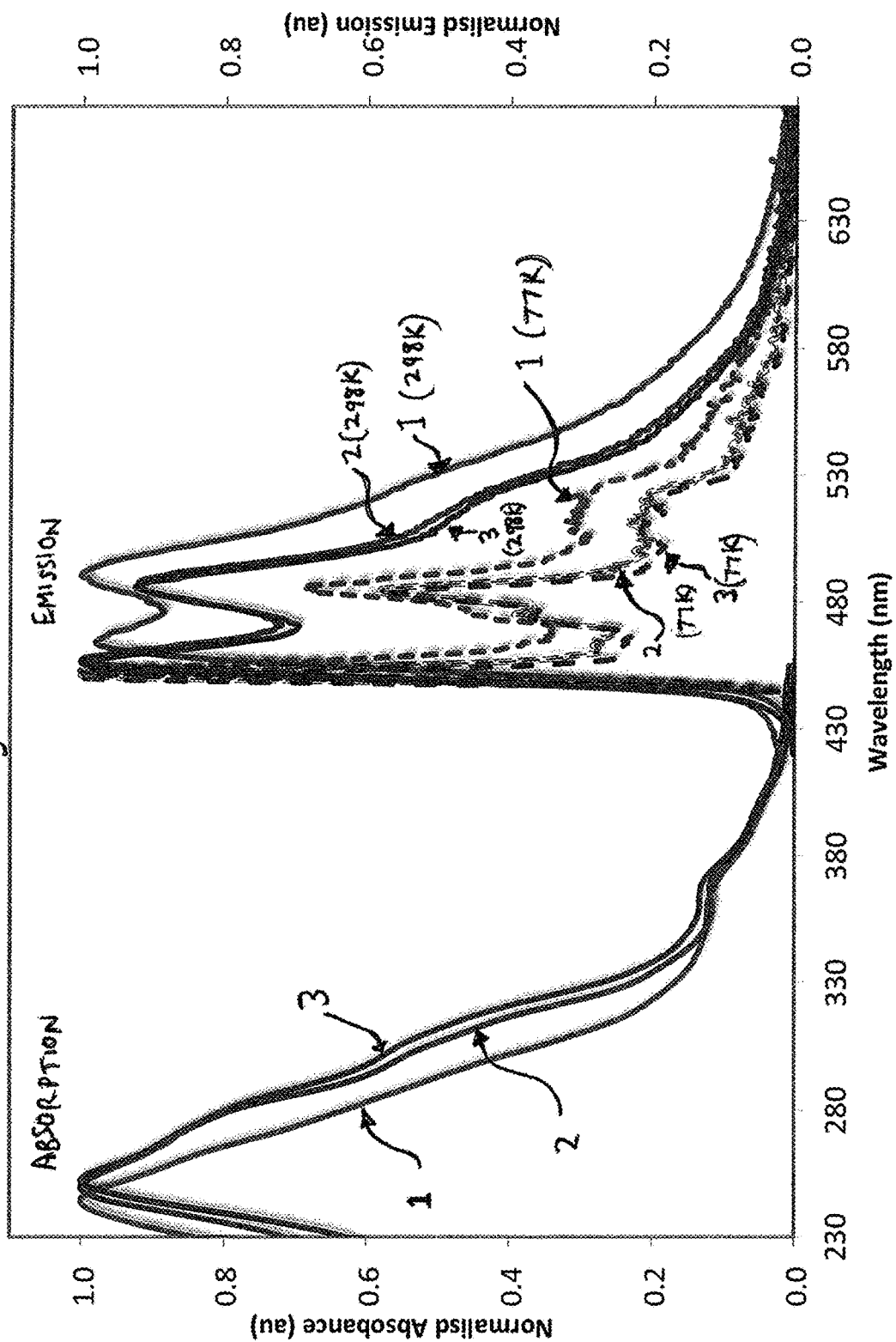
FIG. 1 shows the emission profile of selected iridium complexes.

General Approaches to Ligand and Complex Synthesis and Physical Properties of Complexes The known cyclometalating ligand 2-(2',4'-difluorophenyl)pyridine, (dFppy),

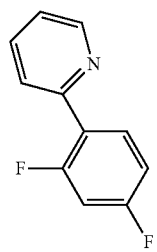 [SMILES: Fc1ccc(-c2ccccn2)c(F)c1]

was chosen as an exemplary ligand (a C^N ligand) to complement ligands according to formula I in the cationic iridium III complexes of the invention.

dFppy is appropriate as it is the most common electron-deficient C^N ligand reported for use in luminescent iridium III complexes.

The dFppy ligand was prepared in good yield by a modified method to that reported previously (reference 2, and see scheme 5 below). The corresponding p-dichlorobridged iridium dimer, [Ir(dFppy)₂Cl]₂, was prepared by the method reported by Nonoyama (reference 3 and see scheme 6 below).

N^N ligands were prepared as indicated below in scheme 5 with more detailed information provided below under the heading Experimental Section. First reference N^N ligand 1H,1H'-2,2'-biimidazole, (biim), was prepared in moderate yield by the condensation of glyoxal in the presence of ammonium acetate (reference 4).

A second reference N^N ligand dMebiim was obtained by alkylation of biim with methyl iodide Ligand Ia 1,1'-(α,α'-o-Xylylene)-2,2-biimidazole (o-Xylbiim) is a ligand (N^N) in accordance with formula I of the invention. It was also obtained by alkylation of biim, using p,p'-dibromo-o-xylene.

Alkylation of biim using methyl iodide in the presence of DMF and aqueous sodium hydroxide base at room temperature (reference 5) afforded dMebiim in good yield while more forcing conditions were required to obtain o-Xylbiim (Scheme 5). (reference 6)

Scheme 5

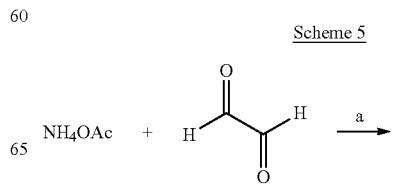

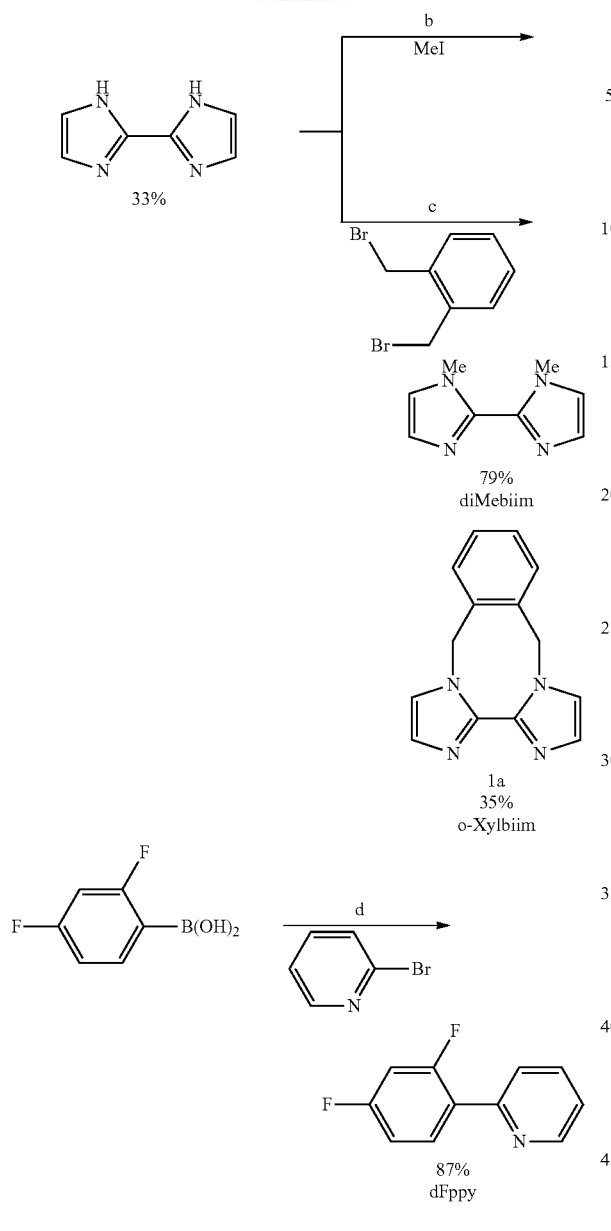
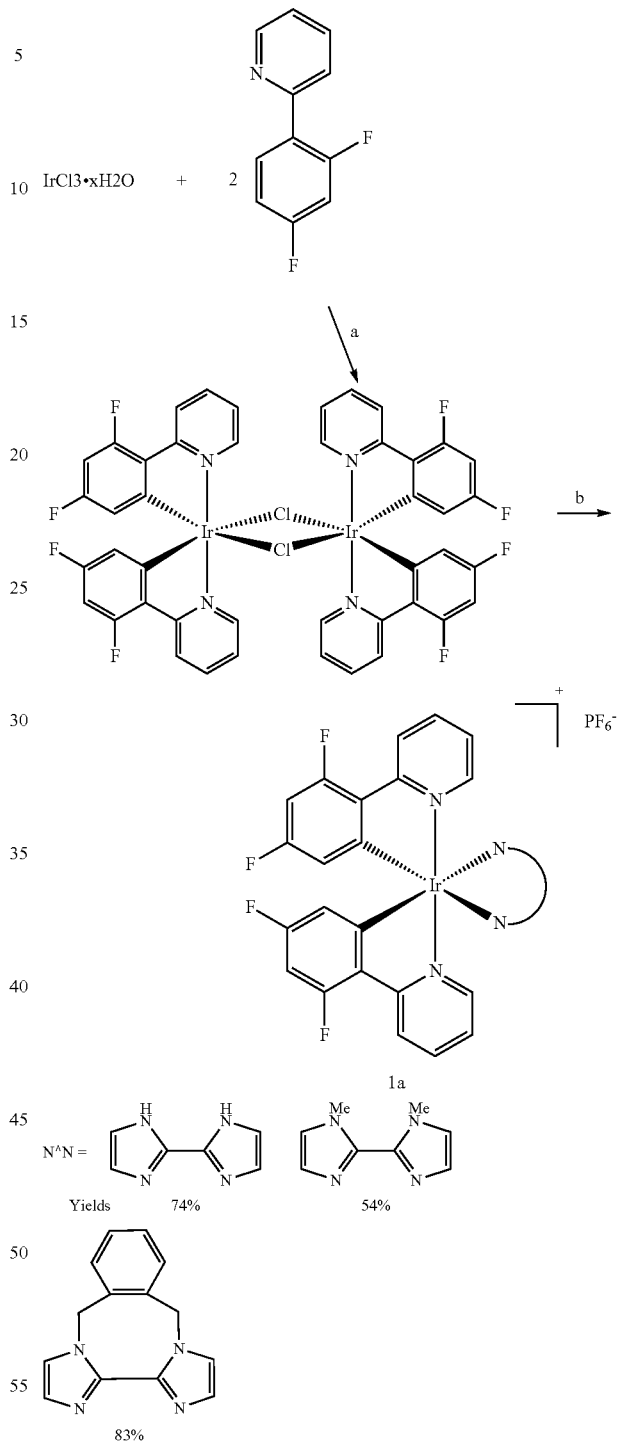

Scheme 5. Synthesis of CˆN and NˆN ligands. Reagents and conditions: [a] H$_2$O, 40° C., 8 h. [b] NaOH (35% w/v), DMF, RT, 12 h. [c] NaOH (35% w/v), MeCN, 82° C., 12 h. [d] 2.0 equiv. Na$_2$CO$_3$, 5 mol % Pd(PPh$_3$)$_4$, N$_2$, 1,4-dioxane/H$_2$O (4:1 v/v), 105° C., 19 h.

The iridium complexes were isolated in good yield by cleavage of [Ir(dFppy)$_2$Cl]$_2$ with the corresponding biimidazole (NˆN ligand) in a refluxing DCM/MeOH solution followed by purification by column chromatography and isolation as the PF$_6^-$ salt by anion metathesis with solid NH$_4$PF$_6$ (Scheme 6, below). The purity and structure of the complexes were established by NMR spectroscopy, HRMS and melting point analyses. The molecular structures of 1 and 3 were determined by single-crystal X-Ray structure analysis.

Reagents and conditions:
a 2-EtOC$_2$H$_4$OH/H$_2$O (4:1 v/v), 110° C., N2, 19 h.
b i. NˆN ligand, CH$_2$Cl$_2$/MeOH (5:4 v/v), 55° C., 19 h, N2; ii. Excess solid NH$_4$PF$_6$.

The reference NˆN ligands and ligand 1a were used together with exemplary CˆN ligand dFppy to prepare iridium complexes (1, 2, 3, below). Reference complexes 1, and 2 are compared to complex 3 of the invention in the following results.

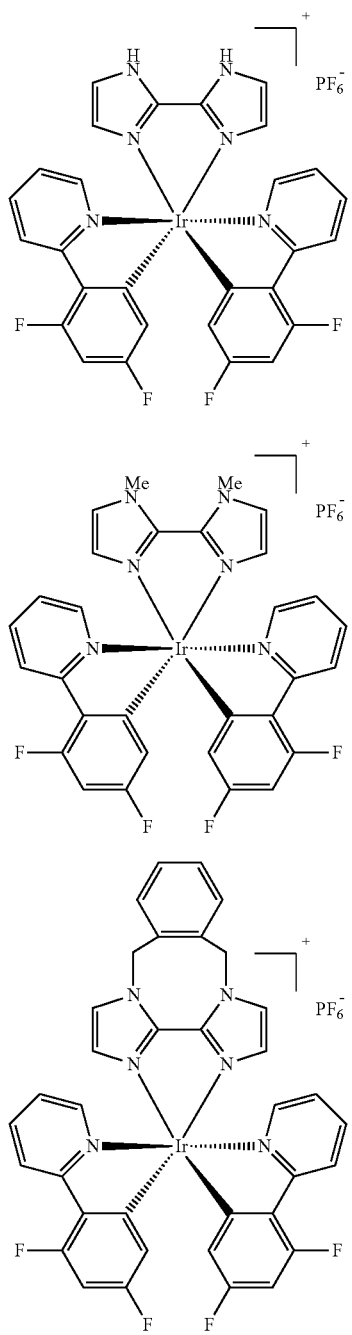

Cyclic Voltammetry.

The electrochemical behavior of complexes 1-3 was investigated by cyclic voltammetry (CV) in deaerated MeCN solution containing n-NBu$_4$PF$_6$ as the supporting electrolyte and using Fd/Fc$^+$ as an internal standard at 298 K. All potentials are referenced with respect to SCE (Fd/Fc$^+$=0.38 V in MeCN) and all reported data were carried out at a scan rate of 50 mV s$^{-1}$. The HOMO energy levels were determined from the relation $E_{HOMO}=-[E^{ox}_{pa\ vs\ Fc/Fc+}+5.39]$ eV, while the lack of a detectable reduction wave in the accessible solvent window necessitated estimating the $E_{LUMO}$ energies from the sum of the $E_{HOMO}$ values and the optical band gap values, $E_{0,0}$, for each complex. $E_{0,0}$ was inferred from the intersection point between the absorption and emission spectra obtained at 298 K in MeOH. Table 1 summarizes the relevant electrochemical data.

TABLE 1

Electrochemical data and orbital energies for 1-3.[a]

| Compound | $E^{ox}_{1/2}$ (V) | $\Delta E_p$ (mV) | $E_{HOMO}$ (eV)[b] | $E_{LUMO}$ (eV)[c] | $E_{0,0}$ (eV)[d] |
|---|---|---|---|---|---|
| 1 | 1.51 | 76 | −6.56 | −3.71 | 2.85 |
| 2 | 1.45 | 79 | −6.50 | −3.64 | 2.86 |
| 3 | 1.44 | 72 | −6.49 | −3.59 | 2.90 |

[a]All measurements were performed at 50 mV s$^{-1}$ in deaerated MeCN solution using Fc/Fc$^+$ as an internal standard, and are referenced with respect to SCE (Fc/Fc$^+$ = 0.38 V in MeCN).
[b]$E_{HOMO} = - [E^{ox}_{pa\ vs\ Fc/Fc+} + 5.39]$ eV.
[c]$E_{LUMO} = E_{HOMO} + E_{0,0}$ eV.
[d]$E_{0,0}$ estimated from the intersection point of the absorption and emission spectra at 298 K in MeOH.

The oxidation potentials of 1-3 are expectedly virtually unchanged across the series, with each complex demonstrating a single, quasi-reversible oxidation wave in the region of 1.5 V.

These oxidation potentials are very similar to that previously reported for [Ir(dFMeppy)$_2$(bpy)]PF$_6$(dFMeppy is 2-(2',4'-difluorophenyl)-4-methylpyridine and bpy is 2,2'-bipyridine), where $E^{ox}_{1/2}$=1.55 V under similar conditions. The oxidation is thus assigned to the Ir$^{III}$/Ir$^{IV}$ redox couple with contribution from the C^N ligands. DFT calculations corroborate this analysis. Surprisingly, despite virtually identical photophysical properties to 1, the electrochemical properties of Kim's [Ir(dFpmpy)$_2$(biim)]$^+$ complex differ somewhat, with a reported $E^{ox}_{1/2}$ value of 1.59 V versus Fc/Fc$^+$ in DCM, resulting in modestly higher reported $E_{HOMO}$ (−6.25 eV) and $E_{LUMO}$ (−3.56 eV) energies (reference 7) The HOMO-LUMO energy gap, estimated from the optical gap ($E_{0,0}$), is however similar (2.69 eV) to those in this study. (dFpmpy is 2-(2',4'-difluorophenyl)-4-methylpyridine).

Solution State Photophysical Behavior

FIG. 1 shows the normalized absorption and emission spectra for complexes 1-3 at room temperature in MeOH, also shows the normalized 77 K emission spectra in a 1:1 MeOH/EtOH glass. The absorption spectra for the complexes are relatively unstructured, typical for iridium-biimidazole complexes, with the intense band at around 250 nm region assigned to spin-allowed ligand centered ($^1$LC)$^1\pi\rightarrow\pi^*$ transitions. All three complexes also demonstrate a distinct lower energy absorption band at about 370 nm, as well as a small tail into the near UV region. These bands are also present in [Ir(dFpmpy)$_2$(biim)]$^+$ and were attributed by Kim to be comprised of a mix of $^3\pi\rightarrow\pi^*$ and spin-allowed and spin-forbidden metal-to-ligand charge transfer ($^1$MLCT) and ($^3$MLCT) transitions. Alkylation of the biim ligand leads to a more structured absorption profile, particularly between 250-370 nm. Excitation spectra for 1-3 reproduce these characteristic features.

The structured emission profiles at 77 K and 298 K arise from a $^3$LC emission (FIG. 1). The absence of any rigidochromic shift in the emission maxima further corroborates the $^3$LC nature of the emission. At both 298 and 77 K, two high-energy emission maxima are observed at around 455 nm and 484 nm, along with lower vibronic emission peaks tailing out to about 650 nm. The near identical emission spectra across the three complexes (1,2,3) verifies that the electronics across this series are essentially unchanging, with only a slight blue shift in emission arising from incorporating the alkyl groups in place of the parent protons.

TABLE 2

| | $\lambda_{em}$ (nm)[b] | | $\Phi_{PL}$ (%)[c] | $\tau_e$ | | $k_r$ | $k_{nr}$ |
|---|---|---|---|---|---|---|---|
| | 77 K | 298 K | 298 K | 77 K (μs) | 298 K (ns) | ($\times 10^5$ s$^{-1}$) | ($\times 10^5$ s$^{-1}$) |
| 1 | 453, 486 | 464, 490 | 20 | 3.682 | 1559 | 1.28 | 5.13 |
| 2 | 451, 484 | 457, 486 | 2 | 3.718 | 91 | 2.20 | 107.69 |
| 3 | 450, 483 | 457, 487 | 68 | 3.956 | 3840 | 1.77 | 0.83 |

[a]298 K measurements in deaerated MeOH and 77 K measurements in 1:1 MeOH/EtOH glass.
[b]Principal emission peaks listed.
[c]Quinine sulfate used as the reference ($\Phi_{PL}$ = 54.6% in 0.5M H$_2$SO$_4$ at 298 K).
$k_r$ and $k_{nr}$ are radiative and non-radiative rate constants respectively and $\tau_e$ is the low temperature emission lifetime.

Though the Stokes shifts for 1-3 are very small, the presence of iridium and the microsecond emission lifetimes point to phosphorescence emission. Low temperature emission lifetimes ($T_e$) of all three complexes in 1:1 MeOH/EtOH glass are similar and are in the range of 3.6-4.0 μs. However, at 298 K while $T_e$ for 1 and 3 remains in the microsecond regime, that for 2 drops significantly to 90 ns, indicative of substantial contributions to $k_{nr}$ for this complex at room temperature. The photoluminescence quantum yield, $\Phi_{PL}$, for 1 is 20% and decreases markedly for 2 to only 2%. The $\Phi_{PL}$ for 3 is a remarkable 68%. This demonstrates the benefit that can be obtained making use of a ligand in accordance with formula I. These figures are reflected in the excited state kinetics. While the radiative rate constants, $k_r$, are similar for 1-3 (ranging from 1.3 to 2.2×10$^5$s$^{-1}$), non radiative $k_{nr}$ values differ dramatically across the series. Complex 2 has a $k_{nr}$ of 107×10$^5$s$^{-1}$, which is two orders of magnitude larger than that calculated for 1 at 5.1×10$^5$ s$^{-1}$. The brightest complex, 3, has a calculated $k_{nr}$ of 0.8×10$^5$ s$^{-1}$, which is six-fold smaller than that of 1.

As an alternative to 2-(2',4'-difluorophenyl)pyridine, (dF-ppy) as the C^N ligand the ligand 2-(2,4-difluorophenyl)-4-(2,4,6-trimethylphenyl)pyridine was also prepared as an exemplary ligand (a C^N ligand) to complement ligands according to formula I in the cationic iridium III complexes of the invention.

2-(2,4-difluorophenyl)-4-(2,4,6-trimethylphenyl)pyridine

As shown in scheme 7 below, this ligand was prepared by a modified version of that in reference 8.

Scheme 7,
Synthesis of 2-(2,4-difluorophenyl)-4-(2,4,6-trimethylphenyl)pyridine.

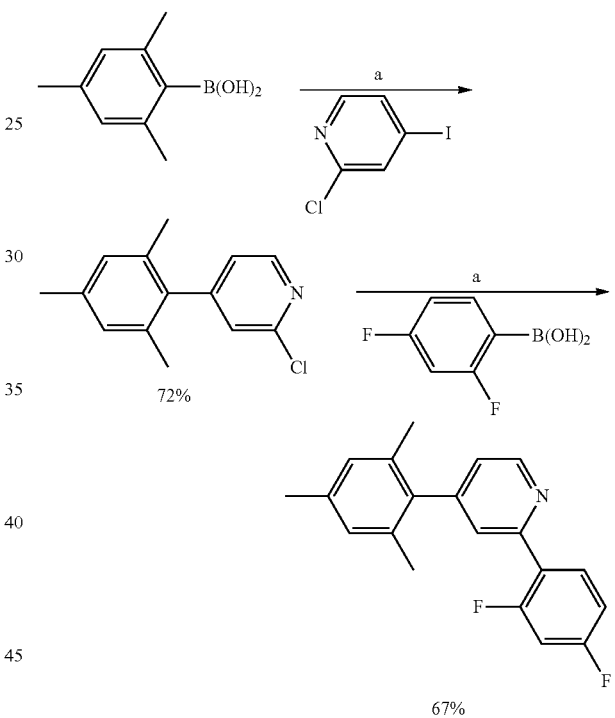

Reagents and conditions:
[a]2.0 equiv. Na$_2$CO$_3$, 5 mol % Pd(PPh$_3$)$_4$, N$_2$, 1,4-dioxane/H$_2$O (4:1 v/v), 105° C., 3 days.
[b]2.0 equiv. Na$_2$CO$_3$, 5 mol % Pd(PPh$_3$)$_4$, N$_2$, 1,4-dioxane/H$_2$O (4:1 v/v), 105° C., 19 h.

An alternative modified route is shown in Scheme 7a.

Scheme 7a: Reagents and conditions:

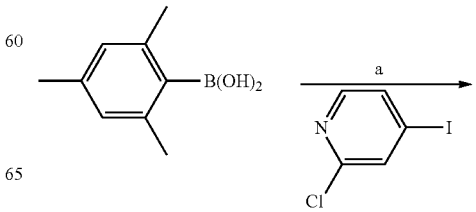

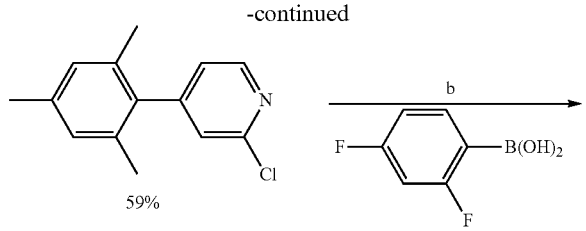

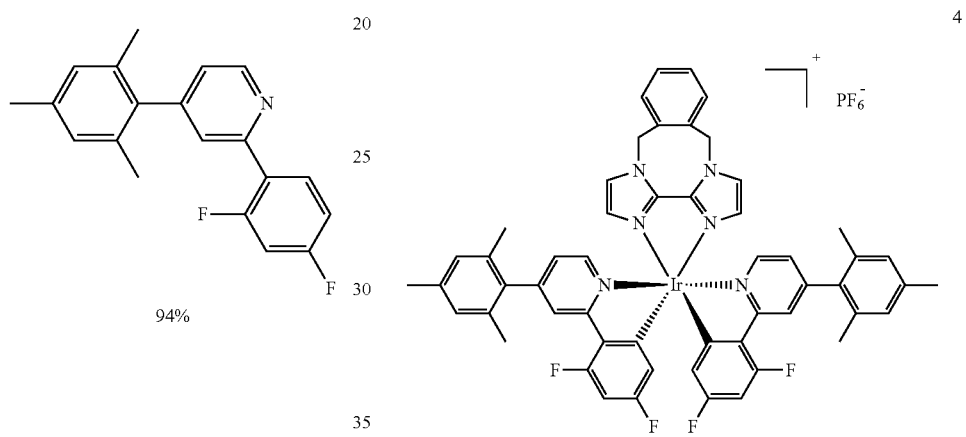

tion step to obtain the desired product in good purity. To facilitate the purification process, adding a large excess of boronic acid (1.5-1.8 equivalents) leads to complete consumption of the starting material. Any side products generated from over cross coupling under these conditions were separable by column chromatography.

This ligand was used to prepare complex 4 in a route analogous to that used to prepare complexes 1 to 3 as described in the Experimental Section, below.

a $K_2CO_3$, 1,4-dioxane/water (2:1 v/v), Pd(PPh$_3$)$_4$ (5 mol %), 100° C., 72 h.
b $Na_2CO_3$, 1,4-dioxane/water (2:1 v/v), Pd(PPh$_3$)$_4$ (5 mol %), 100° C., 19 h.

Mesitylboronic acid is prone to deborylation as a competitive undesired side reaction due to the bulk of the methyl groups in the 2,6-positions. Therefore the starting pyridine tends to be recovered from the reaction. Since the starting pyridine has virtually the same Rf as the product, isolating the desired C^N ligand is not possible by column chromatography alone, requiring an additional Kugelrohr distilla- An alternative synthetic route to the iridium complexes, making use of the known iridium dimer complex [Ir(COD)(p-Cl)]$_2$ (where COD is 1,5-cyclooctadiene) has been found to be beneficial in obtaining higher purity products. This alternative route is shown in scheme 6a below for the manufacture of complex 4.

Scheme 6a. Reagents and conditions:

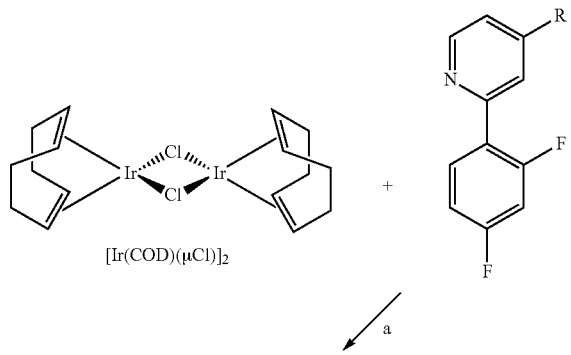

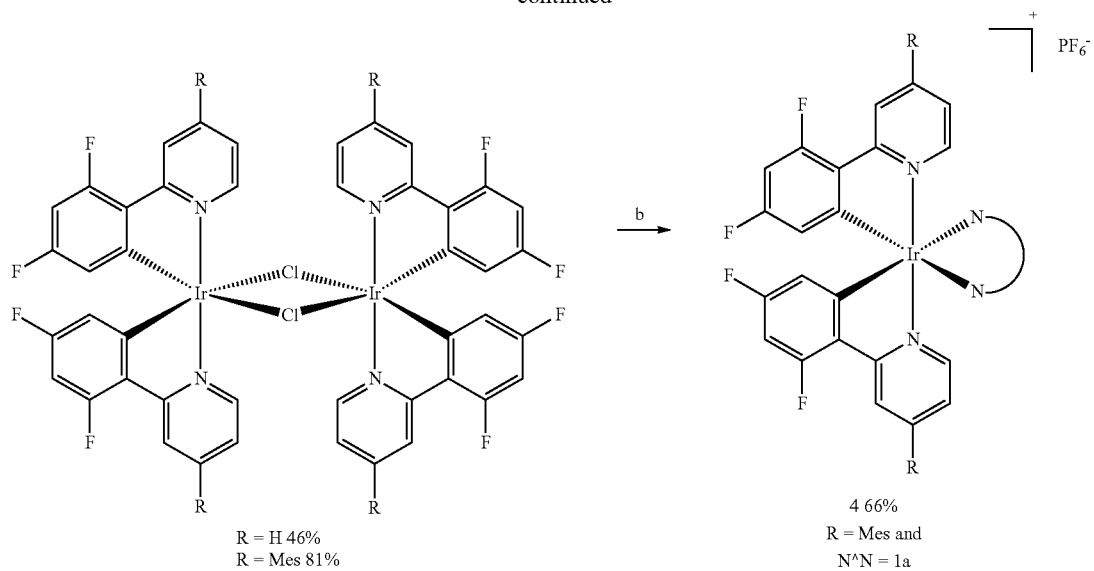

R = H 46%
R = Mes 81%

4 66%
R = Mes and
N^N = 1a a 2-EtOC₂H₄OH, 110° C., N₂, 3 h.
b i. CH₂Cl₂/MeOH (1:1 v/v), 50° C., 19 h, N₂;
ii. Excess NH₄PF₆ (aq).

This complex 4 was determined to have the photo physical properties listed in Table 3, shown in comparison with data for complex 3.

TABLE 3

| Property | Complex 3 | Complex 4 |
|---|---|---|
| $\lambda_{max}$ in MeOH (nm) | 457, 487 | 458, 489 |
| $\lambda_{max}$ in MeCN (nm) | — | 459, 487 |
| Solubility in MeCN | 5 mg in 6 ml | 5 mg in 1 ml |
| $\Phi_{PL}$ in MeOH (%) | 68 | 82 |
| $\Phi_{PL}$ in MeCN (%) | — | 90 |
| $\tau_e$ in MeOH (μs) | 3.84 | 2.26 |
| $\tau_e$ in MeCN (μs) | — | 2.19 |
| $k_{r\ MeOH}$ ($\times 10^5$ s$^{-1}$) | — | 3.36 |
| $k_{r\ MeCN}$ ($\times 10^5$ s$^{-1}$) | — | 4.11 |
| $k_{nr\ MeOH}$ ($\times 10^5$ s$^{-1}$) | — | 0.80 |
| $k_{nr\ MeCN}$ ($\times 10^5$ s$^{-1}$) | — | 0.46 |

FIG. 2 shows the emission spectra in methanol (MeOH) and acetonitrile (MeCN).

TABLE 4

| Complex$^a$ | $\lambda_{em}$ (nm)$^b$ | $\Phi_{PL}$ (%)$^c$ | $\tau_e$ (μs)$^d$ |
|---|---|---|---|
| 4 (neat film) | 465, 492 | 43 | 0.19 (29%), 1.23 (71%) |
| 4 (doped film) | 462, 492 | 89 | 1.92 |

$^a$Neat films were dip coated from MeCN solution while doped films were dip coated from a DCM solution of 5 wt % of the complex in PMMA.
$^b\lambda_{exc}$ at 360 nm.
$^c$Measured using an integrating sphere, with $\lambda_{exc}$ for the neat film performed at 360 nm and for the doped films at 300 nm.
$^c\lambda_{exc}$ at 378 nm.
$^d\lambda_{exc}$ at 378 nm.

Complex 4 is virtually as bright in the solid state ($\Phi_{PL}$: 89% in doped film) as in MeCN solution ($\Phi_N$: 90%), indicating that the rigidifying effects in the solid state are limited for this complex since this has already largely been achieved by the effects of the o-xylbiim ligand. These are remarkably high $\Phi_{PL}$ values for a charged iridium complex in the solid state.

OLED Manufacture

Complex 4 was employed as emitter material in a solution processed OLED constructed as described in more detail in the Experimental Section below. The performance data is given in Table 5.

TABLE 5

| | | OLED performance | | | | |
|---|---|---|---|---|---|---|
| Complex | Turn-on Voltage (V) | Current density (mA/cm$^2$) | Luminance (cd/m$^2$) | EQE (%) | Power efficiency (lm/W) | CIE Coordinates (x, y) |
| 4 | 4.8 | 75 | 1086 | 3.42 | 4.42 | 0.21, 0.37 |

EQE is the external quantum efficiency

Solid State Photophysical Behavior

The complex 4 was further studied in the solid state. Testing of a neat film sample and of a doped film (in PMMA) is summarized below in Table 4.

EXPERIMENTAL SECTION

General Synthetic Procedures. Commercial chemicals were used as supplied. All reactions were performed using standard Schlenk techniques under inert (N₂) atmosphere with reagent grade solvents. Flash column chromatography was performed using silica gel (Silia-P from Silicycle, 60 Å, 40-63 µm). Analytical thin layer chromatography (TLC) was performed with silica plates with aluminum backings (250 µm with indicator F-254). Compounds were visualized under UV light. $^1$H, $^{13}$C and $^{19}$F NMR spectra were recorded on a Bruker Avance spectrometer at 500 MHz, 126 MHz and 471 MHz respectively. The following abbreviations have been used for multiplicity assignments: "s" for singlet, "d" for doublet, "t" for triplet, "m" for multiplet and "br" for broad. Deuterated chloroform (CDCl₃) and deuterated DMSO (DMSO-d₆) were used as the solvents of record. Melting points (Mp's) were recorded using open-ended capillaries on an Electrothermal melting point apparatus and are uncorrected. High-resolution mass spectra were recorded on a quadrupole time-of-flight (ESI-Q-TOF), model ABSciex 5600 Triple TOF in positive electrospray ionization mode and spectra were recorded using sodium formate solution as calibrant. The iridium(III) dimer, [(dFppy)₂Ir(µ-Cl)]₂ was prepared according to the procedure described by Nonoyama.(reference 3).

Ligand Syntheses.

2-(2,4-Difluorophenyl)pyridine (dFppy). 2,4-Difluorophenylboronic acid (1.1 equiv.), 2-bromopyridine (1.0 equiv.), sodium carbonate (2.0 equiv.) were added to a Schlenk tube containing a mixture of 1,4-dioxane and distilled water (4:1 v/v) to obtain a concentration of 0.15 to 0.20 M. The reaction mixture was degassed via three freeze-pump-thaw cycles. Upon warming to room temperature from the third cycle, Pd(PPh₃)₄ (5 mol %) was added to the tube under positive nitrogen pressure and the tube was sealed. The mixture was refluxed for 19 h and then cooled to room temperature. The mixture was poured onto distilled water and extracted multiple times with dichloromethane. The organic fractions were combined, washed with a portion of brine and dried over magnesium sulfate. Filtration and evaporation under reduced pressure gave the crude product (1.45 g). The crude product was purified by flash column chromatography (silica, hexane/ethyl acetate gradient 100:0 to 80:20) to give 1.31 g of pure compound as a colourless oil. Yield: 87%. R$_f$: 0.48 (20% EtOAc/hexanes on silica). $^1$H NMR (500 MHz, CDCl₃) δ (ppm): 8.72 (dt, J=4.5, 1.0 Hz, 1H), 8.03-7.99 (m, 1H), 7.75 (d, J=4.0 Hz, 2H), 7.28-7.23 (m, 1H), 7.03-6.99 (m, 1H), 6.93-6.90 (m, 1H). $^{13}$C NMR (126 MHz, CDCl₃) δ (ppm): 164.6, 162.1, 159.5, 152.7, 149.9, 136.6, 132.3, 124.4, 122.6, 112.1, 104.5. $^{19}$F {$^1$H} NMR (471 MHz, CDCl₃) S (ppm): −109.3 (d, J=6.8 Hz, 1F), −113.0 (d, J=6.8 Hz, 1F). GCMS: (13.6 min) [M]$^+$: 191.

1H,1'H-2,2-biimidazole (biim): To a mixture of ammonium acetate (2.7 equiv.) in distilled water at 40° C. was added dropwise 40% aqueous glyoxal solution (1.0 equiv.) over a period of 3 h to give a concentration of 0.01 M. The mixture was allowed to stir for a further 5 h at room temperature. The reaction mixture was filtered and washed multiple times with distilled water and acetone to give 8.31 g of a brown crude product. This material was added to ethylene glycol (0.5 M), heated to 150° C. and treated with decolourising carbon. Filtration saw product precipitate immediately, with further washings with distilled water to maximise product precipitation. The product was filtered and dried to give 2.47 g as a cream white powder. Yield: 33%. R$_f$: 0.12 (10% MeOH/DCM on silica). Mp: 350-352° C. Litt: >300° C.$^{27a}$ $^1$H NMR (500 MHz, DMSO-d₆) δ (ppm): 12.67 (s, 2H), 7.14 (s, 2H), 7.00 (s, 2H). $^{13}$C NMR (126 MHz, CDCl₃) δ (ppm): 139.8, 128.7, 117.9.

1,1'-Dimethyl-2,2'-biimidazole (dMebiim): 1H,1'H-biimidazole (1.0 equiv.) was added to a mixture of aqueous sodium hydroxide (5.6 equiv., 35% w/v) in DMF to give a concentration of 0.9 M. This was stirred for 1 h. The mixture turned green and then black over the course of the hour. Methyl iodide (3.0 equiv.) was then added slowly to the reaction mixture. The mixture was left to stir for 19 h at room temperature. The crude reaction mixture was then poured onto distilled water and extracted with chloroform multiple times. The combined organic layers were washed with water and dried over sodium sulfate. Filtration and evaporation under reduced pressure gave the crude product (0.29 g). Purification by flash column chromatography (silica, dichloromethane/ethanol gradient 100:0 to 95:5) afforded 0.19 g of the product as an off-white solid. Yield: 79%. R$_f$: 0.25 (10% EtOAc/hexanes on silica). Mp: 117-118° C. $^1$H NMR (500 MHz, CDCl₃) δ (ppm): 7.11 (s, 2H), 6.96 (s, 2H), 4.04 (s, 6H). $^{13}$C NMR (126 MHz, CDCl₃) δ (ppm): 128.0, 122.8, 35.5.

1,1'-(α,α'-o-Xylylene)-2,2-biimidazole (o-Xylbiim): To a solution containing α,α'-dibromo-o-xylene (1.0 equiv.) in acetonitrile (0.1 M) was added with stirring 1H,1'H-biimidazole (1.2 equiv.) followed by aqueous sodium hydroxide (5.6 equiv., 35% v/w) solution. The temperature was increased to reflux, where after about 10 min a yellow-brown solution formed. The mixture was maintained at reflux overnight, before being cooled to room temperature. After addition of distilled water the mixture was extracted with multiple times with dichloromethane. The organic fractions were combined, dried over anhydrous magnesium sulfate and then evaporated to dryness under reduced pressure. The crude product was washed with portions of diethyl ether, affording 0.23 g of the pure compound as an off-white solid. Yield: 35%. Mp: 288-291° C. Litt: 284-292° C.$^{27a}$ $^1$H NMR (500 MHz, DMSO-d₆) δ (ppm): 7.47 (d, J=1.0 Hz, 2H), 7.41-7.47 (m, 4H), 7.11 (d, J=0.5 Hz, 2H), 4.97 (s, 4H). $^{13}$C NMR (126 MHz, CDCl₃) δ (ppm): 139.4, 133.9, 130.1, 128.9, 128.7, 122.1, 49.0.

2-(2,4-Difluorophenyl)-4-(2,4,6-trimethylphenyl)pyridine
2-Chloro-4-(2,4,6-trimethylphenyl)pyridine

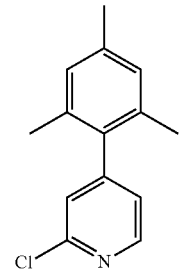

The synthesis of this ligand precursor is a modified version of that outlined in the literature. 2,4,6-trimethylphenylboronic acid (1.5 equiv.) and 2-chloro-4-iodopyridine (1.0 equiv.) were used as the cross-coupling reagents. Following refluxing for 3 days the mixture was cooled to room temperature. Toluene was added and the layers were separated. The organic layer was washed multiple times with water and then dried over magnesium sulphate. The organic solvent was removed under reduced pressure and the product purified by column chromatography (eluent DCM/hexane, 1:5 v/v) and the solvent removed to give the product as a colourless liquid. Yield: 72%. R$_f$: 0.25 (DCM/Hexane 1:5 v/v on silica). $^1$H NMR (400 MHz, CDCl₃) δ (ppm): 8.37

(d, J=4.8 Hz, 1H), 7.10 (s, 1H), 6.97 (dd, J=5.0, 1.6 Hz, 1H), 6.92 (s, 2H), 2.29 (s, 3H), 1.97 (s, 6H).

2-(2,4-Difluorophenyl)-4-(2,4,6-trimethylphenyl)pyridine

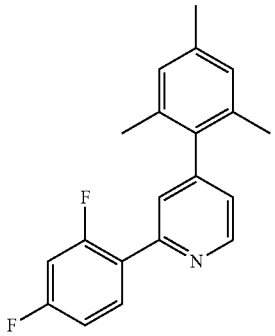 [SMILES: Cc1cc(C)c(-c2ccnc(-c3ccc(F)cc3F)c2)c(C)c1]

The synthesis of this ligand precursor is a modified version of that outlined in the literature. 2,4-Difluorophenylboronic acid (1.1 equiv.) and 2-chloro-4-(2,4,6-trimethylphenyl)pyridine were used as the cross coupling reagents. Upon refluxing for 19 h, the mixture was cooled to room temperature. The mixture was poured onto distilled water and extracted multiple times with dichloromethane. The organic fractions were combined, washed with a portion of brine and dried over magnesium sulfate. Filtration and evaporation under reduced pressure gave the crude product. The crude product was purified by flash column chromatography (eluent DCM/hexane, 1:5 v/v) to give the pure compound as a yellow oil. Yield: 67%. $R_f$: 0.31 (DCM/Hexane 1:5 v/v on silica). $^1$H NMR (400 MHz, CDCl$_3$) δ (ppm): 8.80 (d, J=4.0 Hz, 1H), 8.19 (m, 1H), 7.68 (s, 1H), 7.11 (dd, J=1.2, 4.0 Hz, 1H), 7.05 (m, 1H), 7.02 (s, 2H), 6.91 (m, 1H), 2.39 (s, 3H), 2.11 (s, 6H).

General Procedure for the Synthesis of [(C^N)$_2$Ir(N^N)]PF$_6$ Complexes Described from [Ir(dFppy)$_2$Cl]$_2$ as Precursor Iridium Complex To a Schlenk tube containing [Ir(dFppy)$_2$Cl]$_2$ (1.0 equiv.) and N^N ligand (3.0 equiv.) were added DCM and MeOH (5:4 v/v) to give a concentration of 0.03 M. The mixture was degassed via three freeze-pump-thaw cycles, before backfilling with N$_2$ upon thawing from the third cycle. The reaction mixture was heated to 55° C. for 19 h. Over the course of the reaction the mixture darkened in colour. The solution was cooled to room temperature and solid NH$_4$PF$_6$ (10.0 equiv.) was added and the reaction mixture was left to stir for a further 1 h. The resulting suspension was evaporated to dryness, with the residue then copiously washed with Et$_2$O and distilled water. This crude product was purified by flash column chromatography (silica, DCM/MeOH gradient 100:0 to 95:5). Fractions containing the desired complex were combined and solid NH$_4$PF$_6$ (10 equiv.) was added. The suspension was stirred at room temperature for 0.5 h. This mixture was then evaporated to dryness, washed vigorously with distilled water and dried to afford the pure material.

Iridium (III) bis[2-(4',6'-difluorophenyl)-pyridinato-N,C$^{2'}$]—N,N'-(1H,1'H-2,2'-biimidazole) hexafluorophosphate: [(dFppy)$_2$Ir(biim)](PF$_6$), 1: yellow powder (0.094 g). Yield: 74%. Mp: 310-311° C. $^1$H {$^{19}$F} NMR (500 MHz, DMSO-d$_6$) δ (ppm): 8.24 (d, J=8.5 Hz, 2H), 8.0 (td, J=1.5, 7.8 Hz, 2H), 7.72 (d, J=5.5 Hz, 2H), 7.45 (s, 2H), 7.28 (td, J=1.0, 7.0 Hz, 2H), 6.84 (dd, J=2.0, 8.8 Hz, 2H), 6.55 (d, J=1.0 Hz, 2H), 5.66 (dd, J=2.5, 8.0 Hz, 2H). $^{19}$F {$^1$H} NMR (471 MHz, DMSO-d$_6$) δ (ppm): −70.09 (d, J=712.2 Hz, 6F), −107.72 (d, J=9.42 Hz, 2F), −109.7 (d, J=9.89 Hz, 2F). HR-MS (ES-Q-TOF): [M-PF$_6$]$^+$ Calculated: (C$_{28}$H$_{18}$N$_6$F$_4$Ir) 707.1158. Found: 707.1130.

Iridium (Ill) bis[2(4',6'-difluorophenyl)-pyridinato-N,C$^2$]—N,N'-(1,1-dimethyl-2,2'-biimidazole) hexafluorophosphate: [(dFppy)$_2$Ir(dMebiim)](PF$_6$), 2: yellow powder (0.062 g). Yield: 54%. Mp: 325-326° C. $^1$H {$^{19}$F} NMR (500 MHz, 364 K, DMSO-d$_6$) δ (ppm): 8.25 (d, J=7.5 Hz, 2H), 8.03 (t, J=7.8 Hz, 2H), 7.74 (d, J=6.0 Hz, 2H), 7.53 (d, J=1.5 Hz, 2H), 7.33 (td, J=1.0, 6.5 Hz, 2H), 6.87 (t, J=6.0 Hz, 2H) 6.50 (d, J=1.5 Hz, 2H), 5.63 (dd, J=2.5, 8.0 Hz, 2H) 4.22 (s, 6H). $^{19}$F {$^1$H} NMR (471 MHz, DMSO-d$_6$) δ (ppm): −70.14 (d, J=712.2 Hz, 6F), −107.75 (d, J=9.9, 2F), −109.77 (d, J=9.9, 2F). HR-MS (ES-Q-TOF): [M-PF$_6$]$^+$ Calculated: (C$_{30}$H$_{22}$N$_6$F$_4$Ir) 735.1471. Found: 735.1442.

Iridium (III) bis[2-(4',6'-difluorophenyl)-pyridinato-N,C$^{2'}$]—N,N'-1,1'-(α,α'-o-Xylylene)-2,2-biimidazole hexafluorophosphate: [(dFppy)$_2$Ir(Xylbiim)](PF$_6$), 3: yellow powder (0.062 g). Yield: 83%. Mp: 359-360° C. $^1$H {$^{19}$F} NMR (500 MHz, DMSO-d$_6$) δ (ppm): 8.22 (d, J=8.0 Hz, 2H), 7.97 (t, J=7.5 Hz, 2H), 7.76 (d, J=1.0 Hz, 2H), 7.69-7.57 (m, 3H), 7.56-7.46 (m, 3H), 7.17 (s, br, 2H), 6.79-6.73 (m, 2H), 6.51 (d, J=1.0 Hz, 2H), 5.86 (s, br, 4H), 5.65 (dd, J=2.0, 8.8 Hz, 2H). $^{19}$F {$^1$H} NMR (471 MHz, DMSO-d$_6$) δ (ppm): 70.13 (d, J=712.2 Hz, 6F), −107.60 (m, 2F), −109.7 (m, 2F). HR-MS (ES-Q-TOF): [M-PF$_6$]$^+$ Calculated: (C$_{36}$H$_{24}$N$_6$F$_4$Ir) 809.1628. Found: 809.1597.

Further Example of Iridium Complex Using a Ligand of Formula I

Iridium (III) complex 4 Iridium (III) bis[2-(4',6'-difluorophenyl)4-(2,4,6-trimethylphenyl)pyridinato-N,C2']—N,N'-1,1'-(α,α'-o-Xylylene)-2,2'-biimidazolyl hexafluorophosphate, [Ir(MesdFppy)$_2$(Xylbiim)](PF$_6$)] was prepared by an analogous procedure to that employed for complexes 1 to 3, with the iridium dimer 5 and then complex 4 prepared as shown below.

Synthesis of iridium dimer. Reagents and conditions:

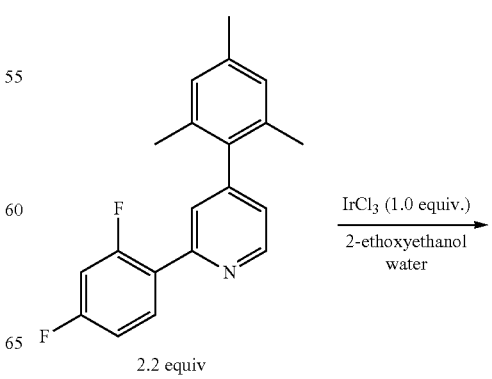

2.2 equiv

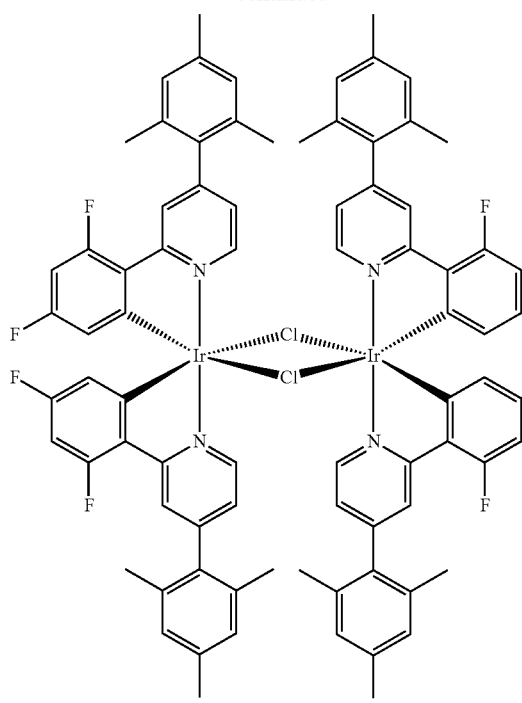

2-Ethoxyethanol/H2O(1:1 v/v), 100° C., 19 h.

Synthesis of iridium complexes. Reagents and conditions:

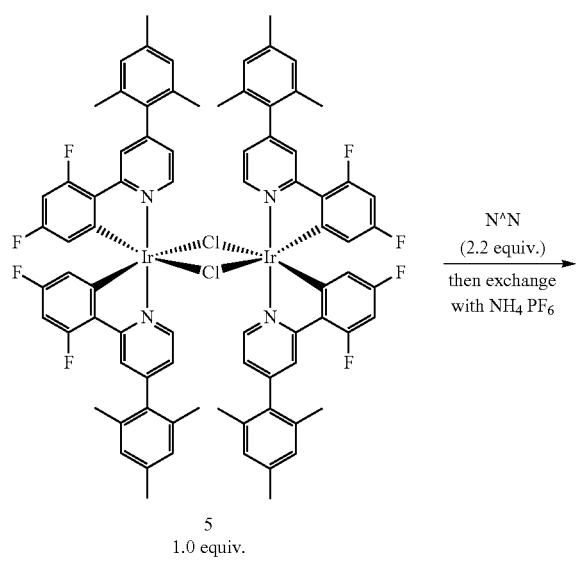

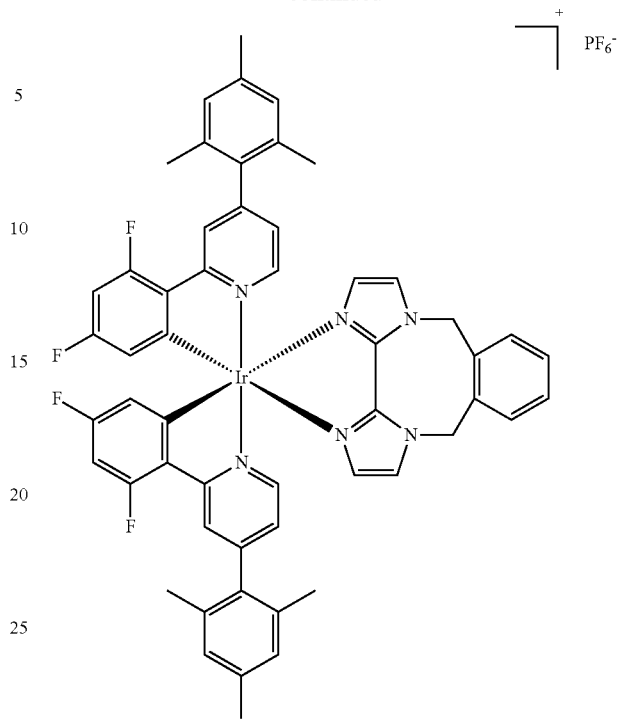

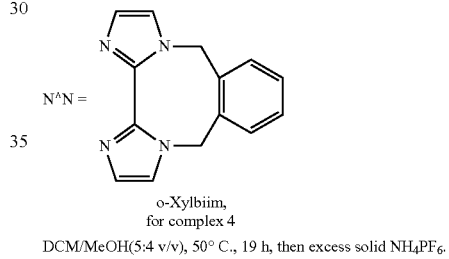

o-Xylbiim,
for complex 4

DCM/MeOH(5:4 v/v), 50° C., 19 h, then excess solid NH4PF6.

Photophysical Measurements.

All samples were prepared in HPLC grade methanol with varying concentrations on the order of μM. Absorption spectra were recorded at RT using a Shimadzu UV-1800 double beam spectrophotometer. Molar absorptivity determination was verified by linear least-squares fit of values obtained from at least three independent solutions at varying concentrations with absorbance ranging from $1.26 \times 10^{-4}$ to $3.43 \times 10^{-5}$ M.

The sample solutions for the emission spectra were prepared in HPLC grade MeOH and degassed via three freeze-pump-thaw cycles. Steady state emission and excitation spectra and time-resolved emission spectra were recorded at 298 K and 77 K using an Edinburgh Instruments F980. All samples for steady state measurements were excited at 360 nm while samples for time-resolved measurements were excited at 378 nm. Emission quantum yields were determined using the optically dilute method (reference 9). A stock solution with absorbance of ca. 0.5 was prepared and then four dilutions were prepared with dilution factors of 5, 6.6, 10 and 20 to obtain solutions with absorbances of ca. 0.1 0.075, 0.05 and 0.025, respectively. The Beer-Lambert law was found to be linear at the concentrations of the solutions. The emission spectra were then measured after the solutions were rigorously degassed via three freeze-pump-thaw cycles prior to spectrum acquisition. For each sample, linearity between absorption and emission intensity was verified through linear regression analysis and additional measurements were acquired until the Pearson regression factor ($R^2$) for the linear fit of the data set surpassed 0.9. Individual relative quantum yield values were calculated for each solution and the values reported represent the slope value. The equation $\Phi_S = \Phi_r (A_r/A_s)(I_s/I_r)(n_s/n_r)_2$ was used to calculate the relative quantum yield of each of the sample, where $\Phi_r$ is the absolute quantum yield of the reference, n is the refractive index of the solvent, A is the absorbance at the excitation wavelength, and I is the integrated area under the corrected emission curve. The subscripts s and r refer to the sample and reference, respectively. A solution of quinine sulfate in 0.5 M $H_2SO_4$ ($\Phi_r$=54.6%) was used as the external reference. (reference 10)

Electrochemistry Measurements.

Cyclic voltammetry (CV) measurements were performed on an Electrochemical Analyzer potentiostat model 600D from CH Instruments. Solutions for cyclic voltammetry were prepared in ACN (acetonitrile) and degassed with ACN-saturated nitrogen bubbling for about 10 min prior to scanning.

Tetra(n-butyl)ammoniumhexafluorophosphate ($TBAPF_6$; ca. 0.1 M in ACN) was used as the supporting electrolyte. An $Ag/Ag^+$ electrode (silver wire in a solution of 0.1 M KCl in $H_2O$) was used as the pseudoreference electrode; a Pt electrode was used for the working electrode and a Pt electrode was used as the counter electrode. The redox potentials are reported relative to a saturated calomel electrode (SCE) electrode with a ferrocenium/ferrocene ($Fc^+/Fc$) redox couple as an internal reference (0.38 V vs SCE). (reference 11)

Fabrication of an OLED

An OLED was constructed of seven layers as illustrated in schematic FIG. 3. The layers are:
1. ITO (Indium Tin Oxide)/2.
2. PEDOT:PSS (poly(3,4-ethylenedioxythiophene) polystyrene sulfonate) (40 nm)/
3. PVK (poly(9-vinylcarbazole) (35 nm)/.
4. mCP+Complex 4+OXD7 (1,3-Bis(N-carbazolyl)benzene+complex 4+2,2'-(1,3-Phenylene)bis[5-(4-tert-butylphenyl)-1,3,4-oxadiazole]) (30 nm)]/.
5. TPBI (2,2',2"-(1,3,5-Benzinetriyl)-tris(1-phenyl-1-H-benzimidazole) (60 nm)/
6. Ca (20 nm)/
7. Al (200 nm)

In the OLED the emitter complex 4 was embedded in an OXD7/mCP mixed host, and sandwiched between the organic layers of PVK and TPBI. PVK facilitates the injection of holes, while the electron transport layer TPBI blocks the holes from penetration into the cathode due to a deep lying HOMO, reducing current leakage. Such a multi-layer structure helps to confine the excitons within the emitting layer as is needed for good OLED performances. Except for TPBI and the contacts, all the layers were deposited by solution-processing methods.

The results of testing the OLED are given in Table 5 above.

REFERENCES 1. a) Yun, S.-J.; Seo, H.-J.; Song, M.; Jin, S.-H.; Kim, Y. I. *Bull. Korean Chem. Soc.* 2012, 33, 3645 b) He, L.; Qiao, J.; Duan, L.; Dong, G.; Zhang, D.; Wang, L.; Qiu, Y. *Adv. Funct. Mater.* 2009, 19, 2950.
2. Campeau, L.-C.; Rousseaux, S.; Fagnou, K. *J. Am. Chem. Soc.* 2005, 127, 18020.
3. Nonoyama, M. *Bull. Chem. Soc. Jpn.* 1974, 47, 767.
4. Thummel, R. P.; Goulle, V.; Chen, B. *J. Org. Chem.* 1989, 54, 3057.
5. Xiao, J.-C.; Shreeve, J. n. M. *J. Org. Chem.* 2005, 70, 3072.
6. Phan, H. V.; Chakraborty, P.; Chen, M.; Calm, Y. M.; Kovnir, K.; Keniley, L. K., Jr.; Hoyt, J. M.; Knowles, E. S.; Besnard, C.; Meisel, M. W.; Hauser, A.; Achim, C.; Shatruk, M. *Chem. Eur. J.* 2012, 18, 15805.
7. Yun, S.-J.; Seo, H.-J.; Song, M.; Jin, S.-H.; Kim, Y. I. *Bull. Korean Chem. Soc.* 2012, 33, 3645.
8. V. N. Kozhevnikov, Y. Zheng, M. Clough, H. A. Al-Attar, G. C. Griffiths, K. Abdullah, S. Raisys, V. Jankus, M. R. Bryce and A. P. Monkman, *Chem. Mater.*, 2013, 25, 2352.
9. (a) Crosby, G. A.; Demas, J. N. *J. Phys. Chem.* 1971, 75, 991; (b) Fery-Forgues, S.; Lavabre, D. *J. Chem. Educ.* 1999, 76, 1260.
10. Melhuish, W. H. *J. Phys. Chem.* 1961, 65, 229.
11. 31) Pavlishchuk, V. V.; Addison, A. W. *Inorg. Chim. Acta* 2000, 298, 97.

What is claimed is:

1. An iridium complex including a ligand according to formula I:

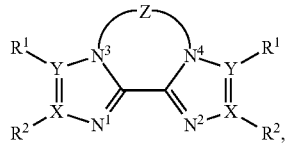

wherein the complex is luminescent, cationic and nitrogen atoms $N^1$ and $N^2$ coordinate to iridium in oxidation state III;

X and Y are independently for each occurrence selected from C or N; and either i) $R^1$ and $R^2$ are independently for each occurrence selected from the group consisting of —H, substituted or unsubstituted primary, secondary or tertiary alkyl, cyclic alkyl, unsaturated alkyl; substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —$S(O)_2R$, —$S(O)_2NR$, —ROC(O)$NR_2$, and ROC(O)N(R)R—, wherein each group R when present on a substituent $R^1$ or $R^2$ is, independently for each occurrence, selected from substituted or unsubstituted alkyl, cyclic alkyl, unsaturated alkyl, substituted or unsubstituted aryl, and substituted or unsubstituted heteroaryl, or $R^1$ and $R^2$ are absent when dictated by the valency of X or Y; or ii) one of the pairs of adjacent $R^1$ and $R^2$ groups is fused to form a ring;

and the other $R^1$ and $R^2$ are independently selected from the group consisting of —H, substituted or unsubstituted primary, secondary or tertiary alkyl, cyclic alkyl, unsaturated alkyl; substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —$S(O)_2R$, —$S(O)_2NR$, —ROC(O)$NR_2$, and ROC(O)N(R)R—, wherein each group R when present on a substituent $R^1$ or $R^2$ is, independently for each occurrence, selected from substituted or unsubstituted alkyl, cyclic alkyl, unsaturated alkyl, substituted or unsubstituted aryl, and substituted or unsubstituted heteroaryl or are absent when dictated by the valency of X or Y; or iii) both pairs of adjacent $R^1$ and $R^2$ groups are each fused to form a ring; and wherein Z is a hydrocarbylene linking group comprising at least two carbon atoms in a chain linking $N^3$ and $N^4$, wherein Z is selected from the group consisting of:

substituted or unsubstituted hydrocarbylene, substituted or unsubstituted unsaturated hydrocarbylene, substituted or unsubstituted hydrocarbylene including one or more heteroatoms replacing one or more carbon atoms in the hydrocarbylene chain, and substituted or unsubstituted unsaturated hydrocarbylene, including one or more heteroatoms replacing one or more carbon atoms in the hydrocarbylene chain.

2. The iridium complex according to claim 1 wherein one of the pairs of adjacent $R^1$ and $R^2$ groups is fused to form a ring.

3. The iridium complex according to claim 1 wherein one of the pairs of adjacent $R^1$ and $R^2$ groups is fused to form a ring, the ring has X and Y as carbon and the ring is selected from the group consisting of substituted or unsubstituted benzene, naphthalene, anthracene, pyrene and fluorene.

4. The iridium complex according to claim 1 wherein one of the pairs of adjacent $R^1$ and $R^2$ groups is fused to form a ring and the ring is heteroaromatic and selected from the group consisting of: substituted or unsubstituted furan, thiophene, pyrrole, oxazole, thiazole, imidazole, isoxazole, isothiazole, pyrazole, pyridine, pyrazine, pyrimidine, triazine, pyrylium, benzo[b]furan, benzo[b]thiophene, indole, 2H-isoindole, benzothiazole and benzothiophene.

5. The iridium complex according to claim 1 wherein both of the pairs of adjacent $R^1$ and $R^2$ groups are each fused to form a ring and the rings have X and Y as carbon and are selected from the group consisting of substituted or unsubstituted benzene, naphthalene, anthracene, pyrene and fluorene.

6. The iridium complex according to claim 1 wherein both of the pairs of adjacent $R^1$ and $R^2$ groups are each fused to form a ring, the rings are heteroaromatic and selected from the group consisting of: substituted or unsubstituted furan, thiophene, pyrrole, oxazole, thiazole, imidazole, isoxazole, isothiazole, pyrazole, pyridine, pyrazine, pyrimidine, triazine, pyrylium, benzo[b]furan, benzo[b]thiophene, indole, 2H-isoindole, benzothiazole and benzothiophene.

7. The iridium complex according to any claim 1 wherein the linking group Z takes the general form:

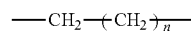

wherein n is from 1 to 5.

8. The iridium complex according to claim 1 wherein the linking group Z is selected from the group consisting of:

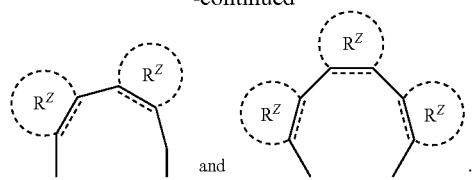

wherein dashed lines in the carbon chain represent, independently for each occurrence, optional unsaturation; and each $R^z$ indicated by dashed part circle is, independently for each occurrence, an optionally present ring of from 3 to 6 atoms.

9. The iridium complex according to claim 8 wherein rings $R^Z$ are present and are selected from the group consisting of saturated, unsaturated, aromatic or heteroaomatic rings of from 3 to 6 atoms.

10. The iridium complex according to claim 9 wherein one or more of rings $R^Z$ is substituted by replacement of one or more H by a substituent selected from the group consisting of:

substituted or unsubstituted primary, secondary or tertiary alkyl, cyclic alkyl, unsaturated alkyl; substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —S(O)$_2$R, —S(O)$_2$NR, —ROC(O)$NR_2$, and ROC(O)N(R)R—, wherein each group R when present is, independently for each occurrence, selected from substituted or unsubstituted alkyl, that may be cyclic and may be saturated or unsaturated, substituted or unsubstituted aryl, and substituted or unsubstituted heteroaryl.

11. The iridium complex according to claim 1 wherein the linking group Z is selected from the group consisting of

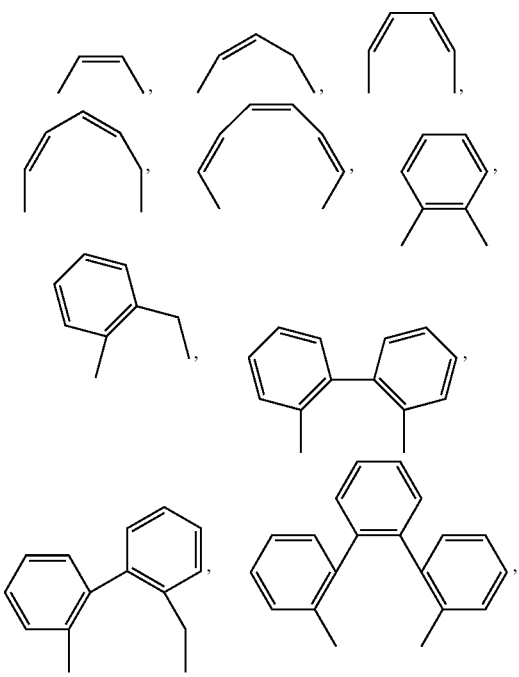

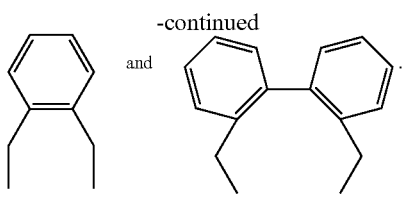 and

12. The iridium complex according to claim 1 wherein the hydrocarbylene linking group Z includes one or more of cyclopentane-1,3-diyl, cyclopentane-1,2-diyl; cyclohexane-1,2-diyl, cyclohexane-1,3-diyl, cyclohexane-1,4-diyl, 1,2-phenylene, 1,3-phenylene and 1,4-phenylene and substituted derivatives thereof.

13. The iridium complex according to claim 1 wherein the ligand of formula I has the structure of one of formulas II, III or IV:

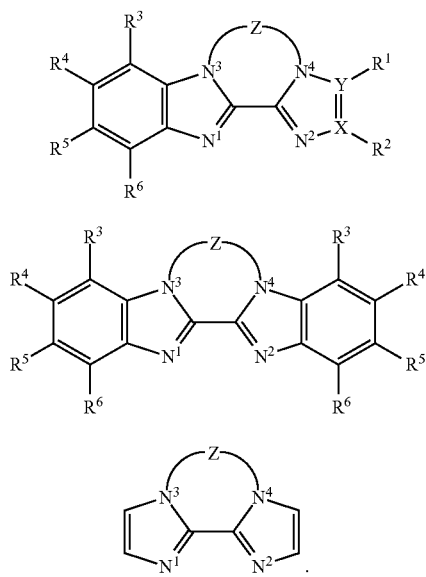

wherein each $R^3$, $R^4$, $R^5$ and $R^6$ is independently for each occurrence selected from the same group of options in claim 1 for $R^1$ and $R^2$.

14. The iridium complex according to claim 1 wherein the complex has the structure of formula V:

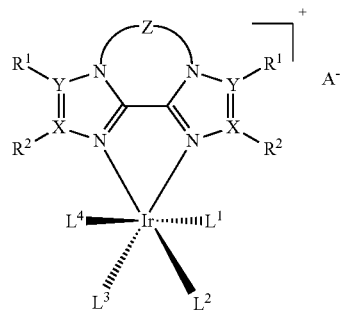

wherein $A^-$ is an anion and $L^1$, $L^2$, $L^3$ and $L^4$ are ligands; and optionally wherein two of ligands $L^1$, $L^2$, $L^3$ and $L^4$ are fused to form a bidentate ligand; or two pairs of $L^1$, $L^2$, $L^3$ and $L^4$ are fused to form two bidentate ligands.

15. The iridium complex according to claim 14 wherein anion $A^-$ is selected from the group consisting of $PF_6^-$ halide, $BF_4^-$, $BR^F_4^-$, $OTf^-$, $OTs^-$, $SbHal_{66}^-NTf_2^-$ $^-NO_3^-$, $CO_3^{2-}$, wherein Hal is halide and $R^F$ is fluoroaryl.

16. The iridium complex according to claim 14 wherein two pairs of $L^1$, $L^2$, $L^3$ and $L^4$ are fused to form two bidentate ligands that are monoanionic cyclometallating bis(chelate) ligands.

17. The iridium complex according to claim 16 wherein the two bidentate ligands are selected from the group consisting of:

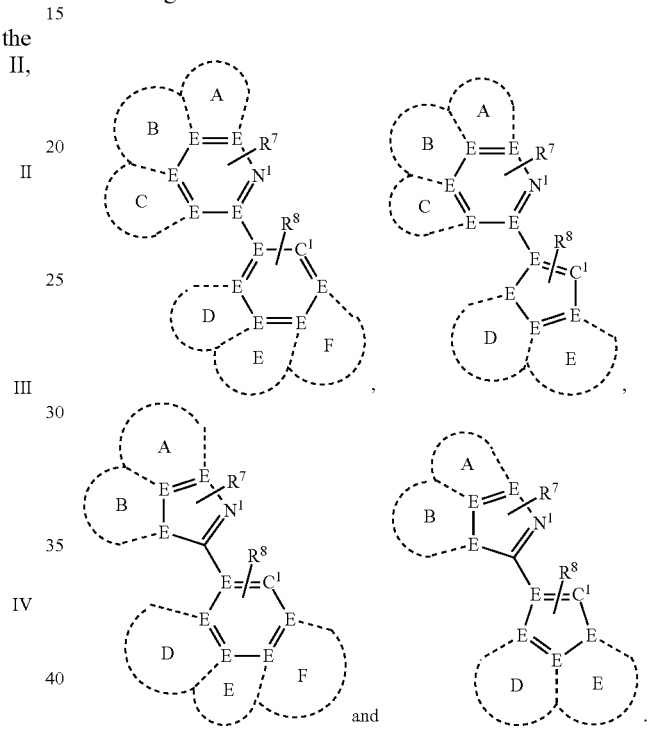

wherein nitrogen atom $N^1$ and carbon atom $C^1$ coordinate to iridium;
ring atoms E are independently for each occurrence selected from the group consisting of C, N, O, and S where valence considerations allow, and when N, may be quaternised with oxygen to form an N oxide;
dashed lines indicate optional substituted or unsubstituted fused rings A to E that may have 3 to 6 atoms that are carbon or, independently for each occurrence N, O, or S where valence considerations allow;
—$R^7$ and —$R^8$ represent optional replacement of at least one —H substituent, where present, of ring atoms E by a substituent independently selected for each occurrence from the group consisting of substituted or unsubstituted primary, secondary or tertiary alkyl, cyclic alkyl, and unsaturated alkyl; substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —S(O)$_2$R, —S(O)$_2$NR, —ROC(O)N$R_2$, and —ROC(O)N(R)R—,
wherein each group R when present on a substituent —$R^7$ or —$R^8$ is, independently for each occurrence, selected from substituted or unsubstituted alkyl, cyclic alkyl, unsaturated alkyl, substituted or unsubstituted aryl, and substituted or unsubstituted heteroaryl.

18. The iridium complex according to claim 17 wherein all ring atoms E are carbon.

19. The iridium complex according to claim 17 wherein the two bidentate ligands are selected from the group consisting of:

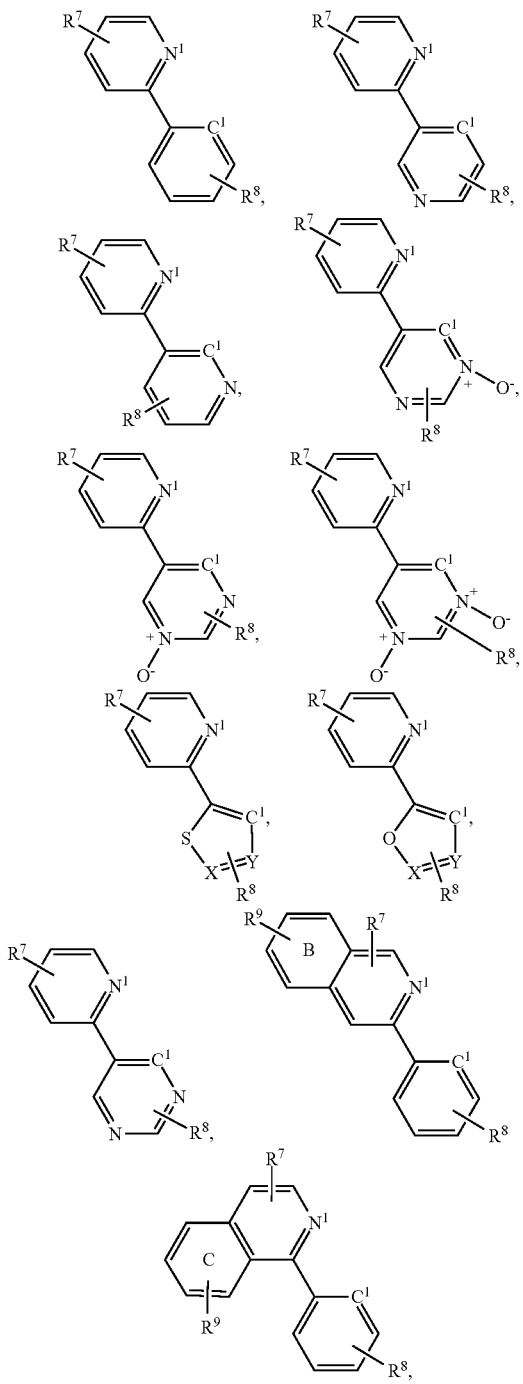

wherein nitrogen atom $N^1$ and carbon atom $C^1$ coordinate to iridium, X and Y have the same meaning as in formula I of claim 1;

wherein —$R^7$ represents optional replacement of one or more of the —H substituents in the ring containing nitrogen atom $N^1$ by a substituent independently selected for each occurrence from the same group of options for $R^1$ and $R^2$ in claim 1;

wherein —$R^9$ represents optional replacement of one or more of the —H substituents in ring B or C, when present, by a substituent independently selected for each occurrence from the same group of options for $R^1$ and $R^2$ in claim 1;

wherein —$R^8$ represents optional replacement of one or more of the —H substituents, when present, in the ring containing coordinating carbon atom $C^1$, by a substituent independently selected for each occurrence from the same group of options for $R^1$ and $R^2$ in claim 1; and wherein one or more carbon atoms in any one or more of: the ring containing nitrogen atom $N^1$; the ring containing coordinating carbon atom $C^1$; and ring B or ring C, may be substituted by N, S or O where valence considerations allow.

20. The iridium complex according to claim 19 wherein the complex is in accordance with formula VI or formula VII:

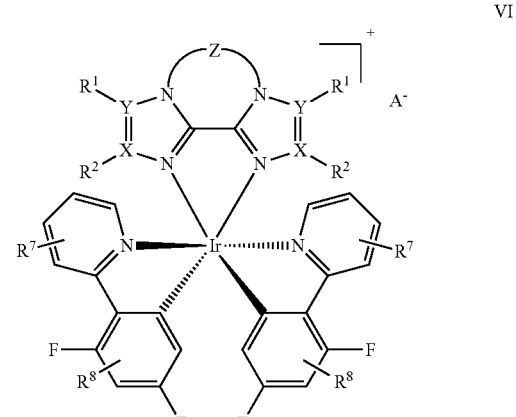

VI

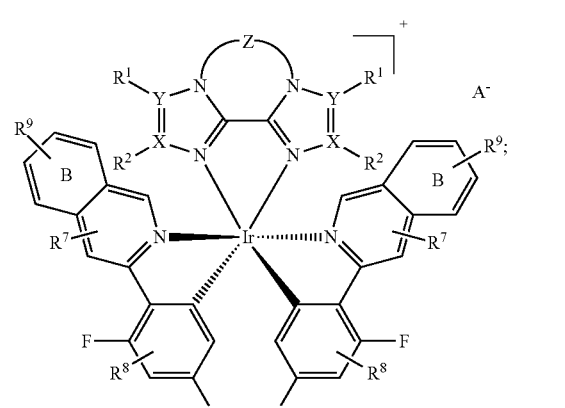

VII wherein A⁻ is an anion; and wherein $R^7$, $R^8$ and $R^9$ have the same meaning as in claim 19, with $R^8$ representing optional further substitution in addition to the two fluorine atoms shown, in the ring containing the coordinating carbon atom.

21. The iridium complex according to claim 1 having structure 3:

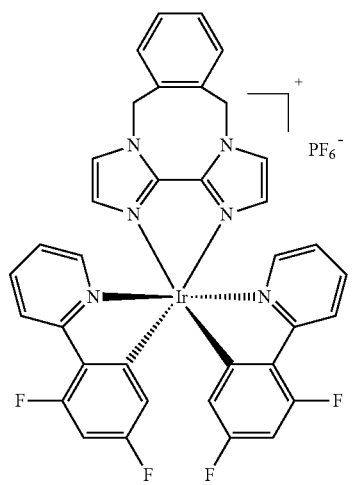

22. The iridium complex according to claim 1 having structure 4:

23. A light emitting device comprising an iridium complex according to claim 1.

24. The light emitting device of claim 23 wherein the light emitting device is a light emitting electrochemical cell.

25. The light emitting device of claim 23 wherein the light emitting device is an organic light emitting diode.

26. The iridium complex according to claim 1 wherein Z includes one or more heteroatoms replacing one or more carbon atoms in the hydrocarbylene chain, and the heteroatoms are independently selected from O, N and S.

27. The iridium complex according to claim 7 wherein the linking group Z contains one or more unsaturations.

28. The iridium complex according to claim 7 wherein one or more of the H in the linking group Z is replaced by a group selected from the group consisting of substituted or unsubstituted primary, secondary or tertiary alkyl, cyclic alkyl, and unsaturated alkyl; substituted or unsubstituted aryl or heteroaryl, halogen, —$CF_3$, —CN, —$SF_5$, —$SO_3$, —S(O)R, —$NO_2$, —$NR_2$, —OR, —C(O)R, —C(O)OR, —C(O)NR, —SR, —C(S)R, —S(O)$_2$R, —S(O)$_2$NR, —ROC(O)$NR_2$, and ROC(O)N(R)R—, wherein each group R when present is, independently for each occurrence, selected from substituted or unsubstituted alkyl, cyclic alkyl, unsaturated alkyl, substituted or unsubstituted aryl, and substituted or unsubstituted heteroaryl.

* * * * *